(12) United States Patent
Okuno

(10) Patent No.: US 8,708,916 B2
(45) Date of Patent: Apr. 29, 2014

(54) ULTRASOUND DIAGNOSTIC APPARTUS WITH CMUT BIAS VOLTAGE DISCHARGE SYSTEM

(75) Inventor: Yoshiyuki Okuno, Fussa (JP)

(73) Assignee: Olympus Medical Systems Corp., Tokyo (JP)

( * ) Notice: Subject to any disclaimer, the term of this patent is extended or adjusted under 35 U.S.C. 154(b) by 158 days.

(21) Appl. No.: 13/204,154

(22) Filed: Aug. 5, 2011

(65) Prior Publication Data

US 2012/0078109 A1     Mar. 29, 2012

Related U.S. Application Data

(63) Continuation of application No. PCT/JP2011/059018, filed on Apr. 11, 2011.

(30) Foreign Application Priority Data

Apr. 15, 2010   (JP) .................................. 2010-094103

(51) Int. Cl.
  *A61B 8/00*   (2006.01)

(52) U.S. Cl.
  USPC ........................................................ 600/459

(58) Field of Classification Search
  None
  See application file for complete search history.

(56) References Cited

U.S. PATENT DOCUMENTS

| | | | |
|---|---|---|---|
| 6,328,696 B1 | 12/2001 | Fraser | |
| 2005/0148873 A1 | 7/2005 | Petersen et al. | |
| 2005/0225916 A1 | 10/2005 | Bolorforosh et al. | |
| 2007/0073154 A1 | 3/2007 | Karasawa | |
| 2007/0167814 A1* | 7/2007 | Wakabayashi et al. | 600/459 |
| 2007/0293763 A1* | 12/2007 | Matsumura | 600/459 |
| 2009/0088646 A1 | 4/2009 | Nagano et al. | |
| 2009/0299192 A1 | 12/2009 | Asafusa et al. | |
| 2009/0301199 A1 | 12/2009 | Azuma et al. | |

FOREIGN PATENT DOCUMENTS

| | | |
|---|---|---|
| EP | 1 932 476 A1 | 6/2008 |
| JP | 7-111692 A | 4/1995 |
| JP | 2000-51213 A | 2/2000 |
| JP | 2001-299759 | 10/2001 |

(Continued)

OTHER PUBLICATIONS

English machine translation of JP 2000-051213, Feb. 22, 2000.*

(Continued)

*Primary Examiner* — Unsu Jung
*Assistant Examiner* — Serkan Akar
(74) *Attorney, Agent, or Firm* — Scully, Scott, Murphy & Presser, P.C.

(57) ABSTRACT

An ultrasound diagnostic system includes a connection section for detachably connecting an ultrasound device mounted with a capacitive micromachined ultrasonic transducer (C-MUT) and a transmission signal generation section that generates a transmission signal using a connector provided in the ultrasound device and a connector receiver provided in the ultrasound observation apparatus, a discharge section for discharging the charge applied to the C-MUT, a lock mechanism that keeps the connection section in a locked state and a released state and a switching section arranged on a signal line between the C-MUT and the ultrasound observation apparatus, wherein when a predetermined mounting state is set, the C-MUT is electrically connected to the transmission signal generation section via the signal line, and through switching by the switching section after an operation of unlocking the lock mechanism, a state is set in which the charge of the C-MUT of the ultrasound device is discharged.

7 Claims, 15 Drawing Sheets

(56) References Cited

FOREIGN PATENT DOCUMENTS

| | | |
|---|---|---|
| JP | 2002-017722 | 1/2002 |
| JP | 2004-503313 | 2/2004 |
| JP | 2008-5885 A | 1/2008 |
| JP | 2008-017937 | 1/2008 |
| JP | 2008-068017 | 3/2008 |
| JP | 2009-082360 | 4/2009 |
| WO | WO 01/97562 A2 | 12/2001 |
| WO | WO 2005/120359 A1 | 12/2005 |
| WO | WO 2007/029357 A1 | 3/2007 |

OTHER PUBLICATIONS

English machine translation of JP 2001-299759, Oct. 30, 2001.*
European Search Report dated Jun. 27, 2012 from corresponding European Patent Application No. EP 11 76 8822.6.

* cited by examiner

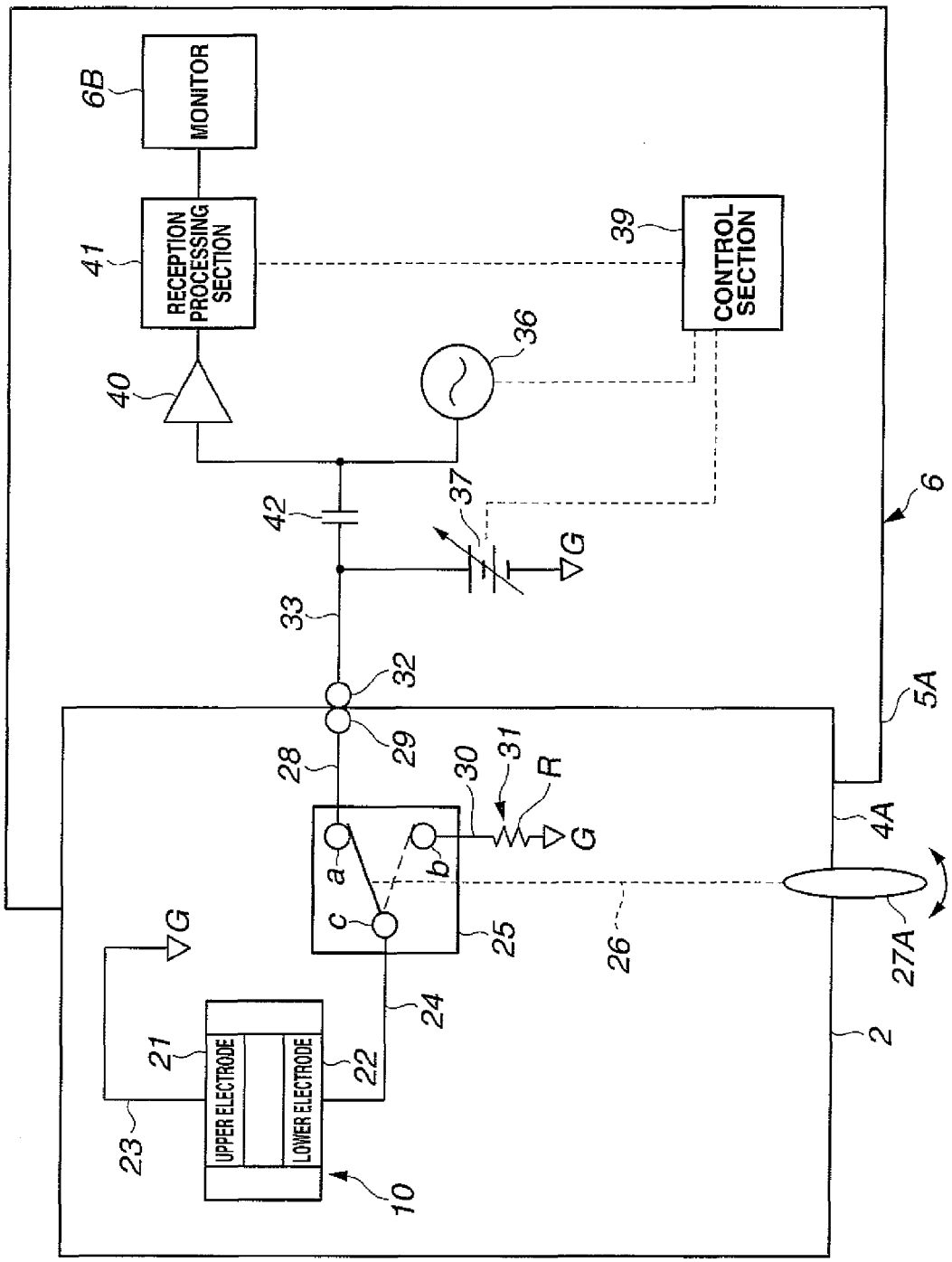

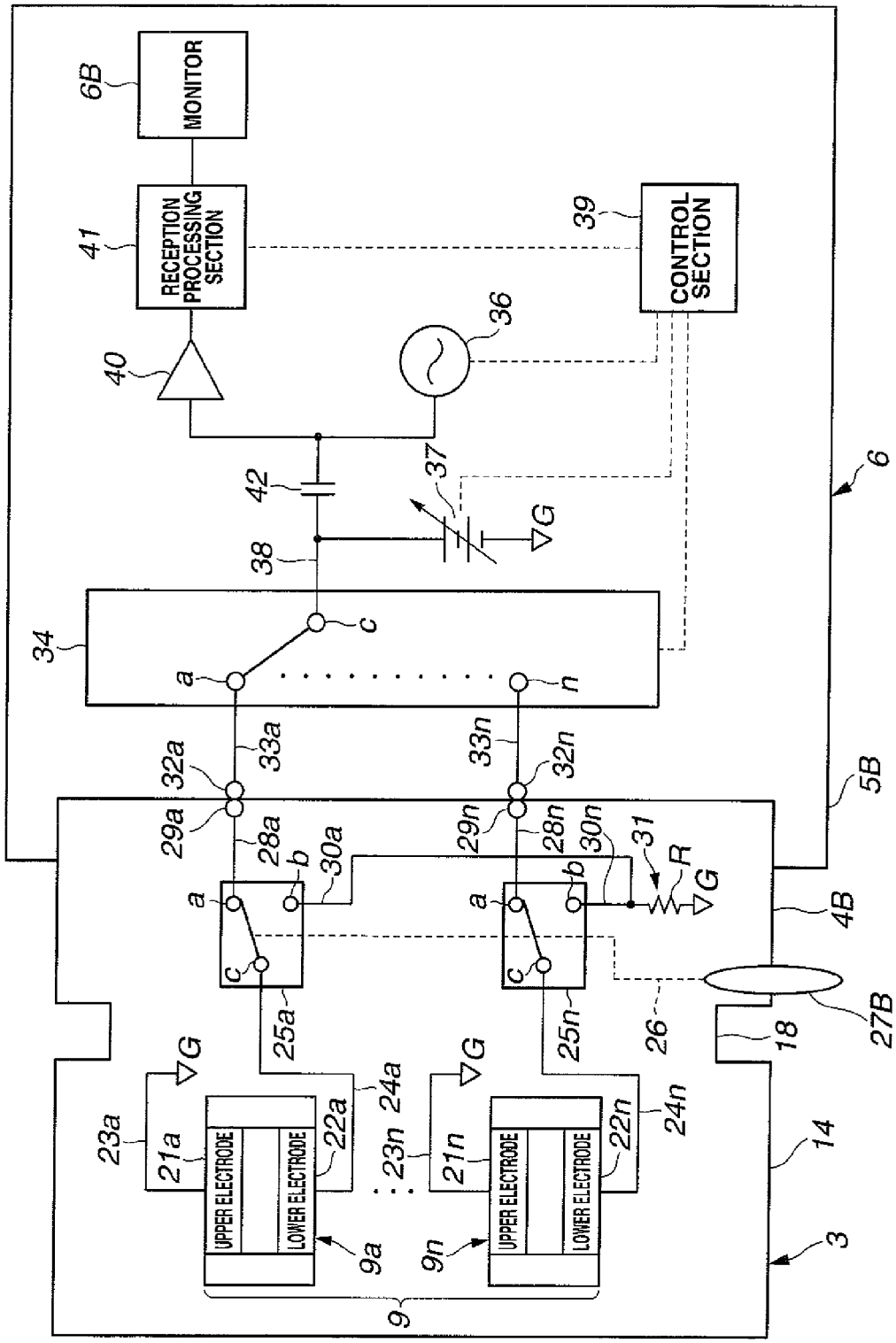

(A)

(B)

(C)

(A)

(B)

(C)

(A)

(B)

(C)

(A)

(B)

ULTRASOUND DIAGNOSTIC APPARTUS WITH CMUT BIAS VOLTAGE DISCHARGE SYSTEM

CROSS REFERENCE TO RELATED APPLICATION

This application is a continuation application of PCT/JP2011/059018 filed on Apr. 11, 2011 and claims benefit of Japanese Application No. 2010-094103 filed in Japan on Apr. 15, 2010, the entire contents of which are incorporated herein by this reference.

BACKGROUND OF THE INVENTION

1. Field of the Invention

The present invention relates to an ultrasound diagnostic system using a capacitive micromachined ultrasonic transducer.

2. Description of the Related Art

An ultrasonic transducer using a capacitive micromachined ultrasonic transducer (hereinafter referred to as "C-MUT"), which is different from a piezoelectric transducer, has recently been developed, and an ultrasound diagnostic system is being proposed which is used for an inspection using ultrasound with an ultrasound probe or ultrasound endoscope mounted with the ultrasonic transducer connected therewith.

The C-MUT has a structure in which one cavity is provided in a silicon substrate and electrodes are provided on and below the cavity, and by applying an ultrasound drive signal (or transmission signal) together with a bias voltage to these electrodes, a film above the cavity is made to vibrate to transmit ultrasound, a returned echo signal is detected with the upper film and transmission/reception of ultrasound is thereby realized.

Since the C-MUT has a structure using a capacitive micromachined ultrasonic transducer, the C-MUT is liable to store charge and when the C-MUT continuously drives ultrasound for a long time, a certain amount of charge is accumulated.

In order to alleviate disadvantages of the deterioration in electric acoustic conversion efficiency in the upper film due to the accumulation of charge, International Publication No. 2007/029357 as a first related art discloses that sensitivity during transmission/reception is corrected by monitoring the amount of charge.

Furthermore, as a second related art, International Publication No. 2005/120359 discloses means for adjusting a DC bias voltage when the DC bias voltage is superimposed on a high frequency pulse as a transmission signal and applied to the C-MUT.

SUMMARY OF THE INVENTION

An ultrasound diagnostic system according to one aspect of the present invention includes an ultrasound device mounted with a capacitive micromachined ultrasonic transducer, a connection section for detachably connecting the ultrasound device and an ultrasound observation apparatus provided with a transmission signal generation section that generates a transmission signal to drive the capacitive micromachined ultrasonic transducer using a connector provided in the ultrasound device and a connector receiver provided in the ultrasound observation apparatus, a discharge section for discharging the charge applied to the capacitive micromachined ultrasonic transducer, a lock mechanism that keeps, when the connector is set in a predetermined mounting state with respect to the connector receiver, a locked state in which the connector is prevented from disconnecting from the connector receiver, and that sets a released state in which the locked state is released through an unlock operation and a switching section arranged on a signal line between the capacitive micromachined ultrasonic transducer and the ultrasound observation apparatus, wherein when the predetermined mounting state is set, the capacitive micromachined ultrasonic transducer is electrically connected to the transmission signal generation section via the signal line, and through switching of the switching section after the unlock operation with respect to the lock mechanism, a state is set in which the charge of the capacitive micromachined ultrasonic transducer in the ultrasound device that can be disconnected from the ultrasound observation apparatus is discharged by the discharge section.

BRIEF DESCRIPTION OF THE DRAWINGS

FIG. 2A is a configuration diagram illustrating an internal configuration of an electric system of an observation apparatus and an ultrasound probe unit of the first embodiment;

FIG. 2B is a configuration diagram illustrating an internal configuration of an electric system of the observation apparatus and an ultrasound endoscope of the first embodiment;

DETAILED DESCRIPTION OF THE PREFERRED EMBODIMENTS

Hereinafter, embodiments of the present invention will be described with reference to the accompanying drawings.

First Embodiment

Figure 1:
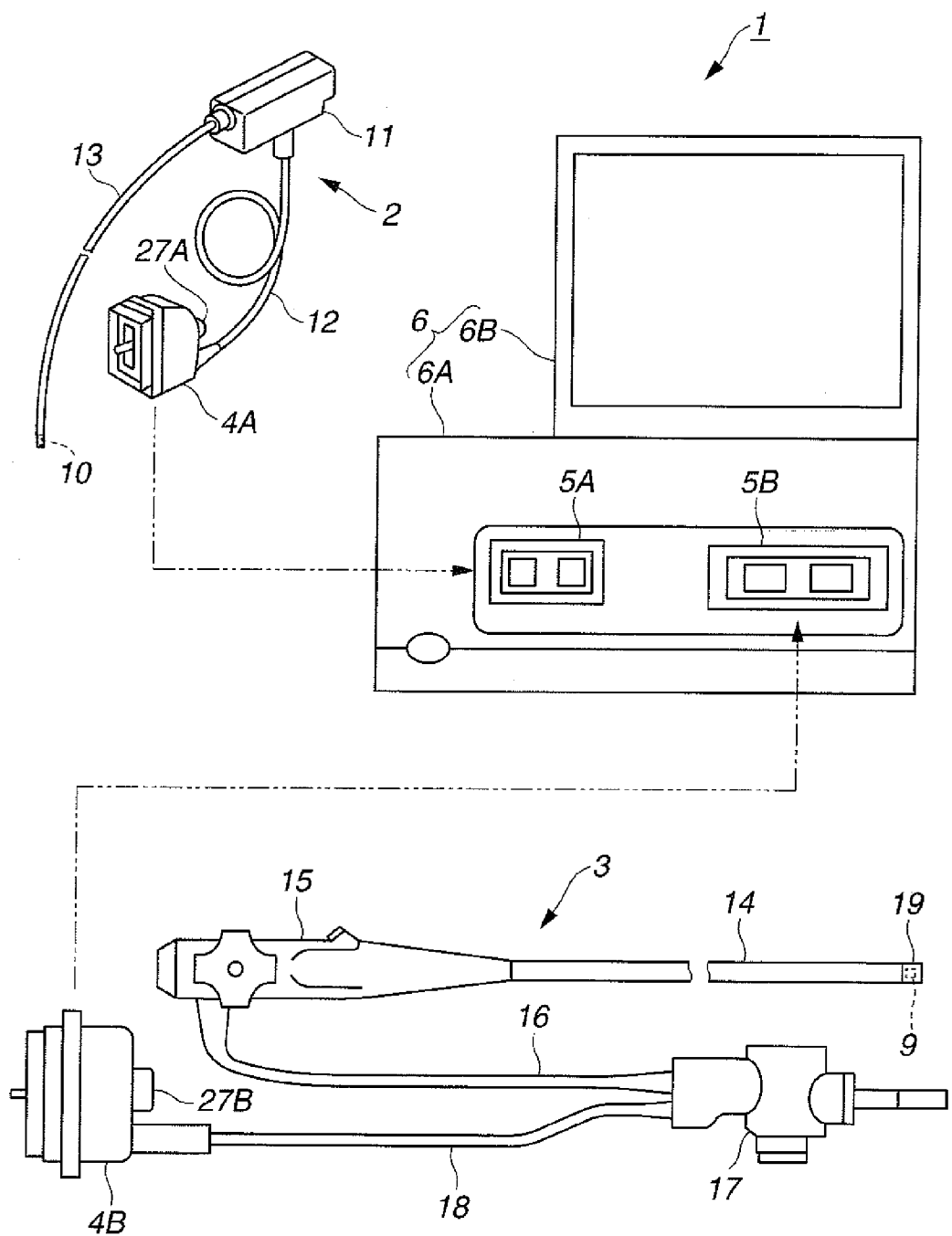
FIG. 1 is a schematic diagram illustrating an overall configuration of an ultrasound diagnostic system according to a first embodiment of the present invention.

FIG. 1 illustrates an overall configuration of an ultrasound diagnostic system 1 according to a first embodiment of the present invention. The ultrasound diagnostic system 1 includes an ultrasound probe unit 2 as an ultrasound device for inspecting a subject using ultrasound and an ultrasound endoscope 3 as an ultrasound device inserted into the body cavity of the subject and provided with a function of performing an inspection using ultrasound and an endoscope function.

Furthermore, the ultrasound diagnostic system 1 is provided with connector receivers 5A and 5B constituting connection sections to which connectors 4A and 4B of the ultrasound probe unit 2 and the ultrasound endoscope 3 are detachably connected and is also constructed of an ultrasound observation apparatus body (hereinafter simply abbreviated as "observation apparatus body") 6A provided with a transmission/reception signal processing system that transmits/receives ultrasound and a monitor 6B as a display apparatus. The observation apparatus body 6A and the monitor 6B constitute an observation apparatus 6.

The ultrasound probe unit 2 includes an ultrasound probe 13 incorporating, for example, a mechanical scan capacitive micromachined ultrasonic transducer (hereinafter abbreviated as "C-MUT") 10 as an ultrasonic transducer for transmitting/receiving ultrasound, an ultrasound probe drive unit (hereinafter abbreviated as "drive unit") 11 to which the ultrasound probe 13 is detachably connected and a cable section 12 that extends from the drive unit 11. The connector 4A detachably connected to the above described connector receiver 5A is provided at an end of the cable section 12. The connector receiver 5A constitutes a connection section to which an ultrasound device driven according to a mechanical scan scheme such as the ultrasound probe unit 2 is detachably connected.

On the other hand, the above described connector receiver 5B constitutes a connection section of an ultrasound device driven according to an electronic scan such as the ultrasound endoscope 3.

The ultrasound endoscope 3 is provided with an insertion portion 14 inserted into the body cavity of the subject, an operation section 15 provided at a rear end (proximal end) of the insertion portion 14 and a universal cable section 16 that extends from the operation section 15.

An endoscope connector 17 connected to an endoscope light source device (not shown) and a processor is provided at an end of the universal cable section 16. A cable section 18 extends from the endoscope connector 17 and the connector 4B detachably connected to the above described connector receiver 5B is provided at an end of the cable section 18.

For example, an electronic scan C-MUT 9 as an ultrasonic transducer for transmitting/receiving ultrasound is provided at a distal end portion 19 provided at a distal end of the insertion portion 14 of the above described ultrasound endoscope 3.

A C-MUT 10 mounted at a distal end portion of the ultrasound probe 13 in the ultrasound probe unit 2 performs, for example, radial mechanical scan and the C-MUT 9 mounted on the ultrasound endoscope 3 performs, for example, sector electronic scan.

FIG. 2A illustrates an internal configuration of the electric system of the ultrasound probe unit 2 and the observation apparatus 6 in an operating state and FIG. 2B illustrates an internal configuration of the electric system of the ultrasound endoscope 3 and the observation apparatus 6 in an operating state.

As shown in FIG. 2B, in (the distal end portion 19 of) the insertion portion 14 of the ultrasound endoscope 3, for example, a plurality of C-MUT elements $9a, \ldots, 9n$ are arranged along a curved surface to form the sector electronic scan C-MUT 9.

In each C-MUT element $9i$ (i=a, ..., n), an upper electrode $21i$ and a lower electrode $22i$ are formed facing each other across a cavity. The upper electrode $21i$ in each C-MUT element $9i$ is connected to a ground (G in FIG. 2B), that is, grounded via a signal line $23i$.

On the other hand, a DC bias voltage and a transmission signal (also referred to as "drive signal") are applied to the lower electrode $22i$ from the observation apparatus 6 via a signal line $24i$ in the operating state shown in FIG. 2B.

In the present embodiment, the signal line $24i$, one end of which is connected to the lower electrode $22i$ is connected to a common contact c of a switch $25i$ provided, for example, in the connector 4B and the common contact c of each switch $25i$ is selectively connected with one of two contacts a and b.

Each switch $25i$ is connected to a lever 27B that operates to connect or disconnect the ultrasound endoscope 3 to/from the observation apparatus 6 via a connection section 26.

Furthermore, the contact a of each switch $25i$ is connected to a connection contact $29i$ of the connector 4B via a signal line $28i$ and the contact b of each switch $25i$ is connected to one end of a signal line $30i$ and the signal line $30i$ is connected to the ground, that is, grounded via a resistor R making up a discharge section 31.

On the other hand, the connector receiver 5B of the observation apparatus 6 is provided with a connection contact $32i$ connected to the above described connection contact $29i$ and each connection contact $32i$ is connected to a contact i of the multiplexer 34 via a signal line $33i$.

The contact i of the multiplexer 34 is selectively connected to the common contact c sequentially from contact a to n under the switching control of a control section 39. The common contact c is connected to one end of a signal line 38.

Furthermore, the observation apparatus 6 includes a transmission signal generation section 36 that generates a transmission signal (drive signal) for sequentially driving each C-MUT element 9*i* making up the above described C-MUT 9 and transmitting ultrasound in a sector form. Furthermore, the observation apparatus 6 includes a DC bias voltage generation section 37 that generates a DC bias voltage to be superimposed on the transmission signal and outputs the transmission signal and the DC bias voltage to the ultrasound endoscope 3 side via the signal line 38, multiplexer 34 or the like.

When an operator operates a DC bias voltage adjustment knob or the like, the DC bias voltage generation section 37 generates a DC bias voltage of an adjusted value. The DC bias voltage generation section 37 may also be enabled to adjust a DC bias voltage generated under the control of the control section 39.

Furthermore, the observation apparatus 6 includes an amplifier 40 that amplifies an ultrasound echo signal (simply referred to as "echo signal") as a received signal received by each C-MUT element 9*i* of the C-MUT 9 and converted from ultrasound to an electric signal and a reception processing section 41 that performs signal processing on the echo signal as the received signal and generates a video signal.

The video signal outputted from the reception processing section 41 is outputted to the monitor 6B as display means and the monitor 6B displays an ultrasound tomographic image corresponding to the video signal.

Furthermore, a capacitor 42 is provided at some midpoint on the signal line 38 which prevents the DC bias voltage of the DC bias voltage generation section 37 from being applied to the transmission signal generation section 36 and the amplifier 40. The control section 39 controls operations of the transmission signal generation section 36, the DC bias voltage generation section 37, the reception processing section 41 and the like.

Figure 2C:
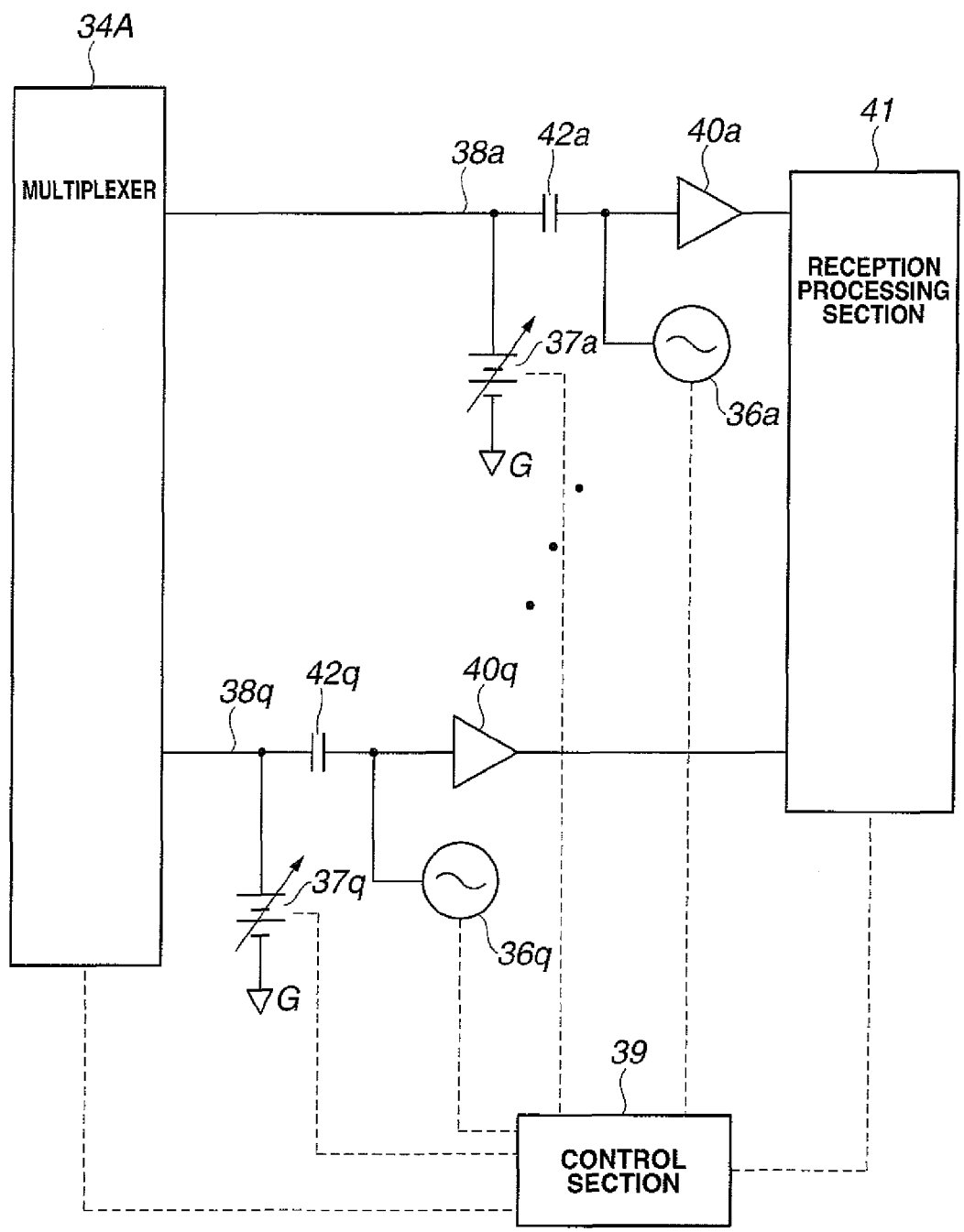
FIG. 2C is a configuration diagram illustrating a configuration example of a peripheral section of a transmission signal generation section of an observation apparatus in a modification example in the case of an electronic scan.

In the observation apparatus 6 according to the electronic scan shown in FIG. 2B, the transmission signal generation section 36 may also be constructed of, for example, a plurality of transmission signal generation sections 36*a*, . . . 36*q* as shown in FIG. 2C, and similarly the amplifier 40 in FIG. 2B may also be constructed of a plurality of amplifiers 40*a*, . . . 40*q* as shown in FIG. 2C.

A configuration may also be adopted in which transmission signal generation timings of the plurality of transmission signal generation sections 36*a*, . . . 36*q* may be shifted so that the plurality of C-MUT elements 9*i* are simultaneously driven via the capacitors 42*a*, . . . 42*q* and the multiplexer 34A.

Furthermore, in this case, echo signals received by the plurality of C-MUT elements 9*i* are amplified by the amplifiers 40*a*, . . . 40*q* and outputted to the reception processing section 41. This makes it possible to scan or cause to converge ultrasound in a direction different from the array shape of the plurality of C-MUT elements 9*a*, 9*b*, . . . 9*n*.

In this case, the DC bias voltage generation section 37 in FIG. 2B may be constructed of a plurality of DC bias voltage generation sections 37*a*, . . . 37*q* as shown in FIG. 2C and the multiplexer 34A may also be constructed so as to switch between signal lines 38*i* in units of a plurality of signal lines. The configuration in FIG. 2C may also be applied to other embodiments in FIG. 9 or the like as will be described later.

On the other hand, in the case of the ultrasound probe unit 2 shown in FIG. 2A, one C-MUT 10 is arranged inside the ultrasound probe 13 and the C-MUT 10 is driven to rotate by a motor (not shown) or the like and ultrasound is then radially subjected to radial mechanical scanning.

The C-MUT 10 has a configuration corresponding to one C-MUT element 9*i* in the C-MUT 9 in FIG. 2B. That is, in the C-MUT 10, an upper electrode 21 and a lower electrode 22 are formed so as to face each other across the cavity. The upper electrode 21 in the C-MUT 10 is connected to the ground (G in FIG. 2A), that is, grounded via the signal line 23.

On the other hand, in the operating state shown in FIG. 2A, a DC bias voltage and a transmission signal are applied to the lower electrode 22 from the observation apparatus 6 side via a signal line 24.

In the present embodiment, the signal line 24, one end of which is connected to the lower electrode 22, is connected, for example, to a common contact c of a switch 25 provided in a connector 4A and the common contact c of the switch 25 is selectively connected to one of the two contacts a and b.

The switch 25 is connected to a lever 27A that connects or disconnects the ultrasound probe unit 2 to/from the observation apparatus 6 via a connection section 26.

Furthermore, the contact a of the switch 25 is connected to a connection contact 29 of the connector 4A via a signal line 28, the contact b of the switch 25 is connected to one end of a signal line 30, and the signal line 30 is connected to the ground, that is, grounded via a resistor R making up a discharge section 31.

On the other hand, a connector receiver 5A of the observation apparatus 6 is provided with a connection contact 32 connected to the above described connection contact 29 and the connection contact 32 is connected to a DC bias voltage generation section 37 via a signal line 33.

Furthermore, the observation apparatus 6 includes a transmission signal generation section 36 that generates a transmission signal (drive signal) for driving the above described C-MUT 10 to transmit ultrasound and the DC bias voltage generation section 37 that generates a DC bias voltage to be superimposed on the transmission signal, and outputs the transmission signal and the DC bias voltage to the ultrasound probe unit 2 side via the signal line 33.

Furthermore, the observation apparatus 6 includes an amplifier 40 that amplifies an echo signal as a received signal received by the C-MUT 10 and converted from ultrasound to an electric signal and a reception processing section 41 that performs signal processing on the echo signal and generates a video signal.

A video signal outputted from the reception processing section 41 is outputted to a monitor 6B as display means and the monitor 6B displays an ultrasound tomographic image corresponding to the video signal.

Furthermore, a capacitor 42 is provided at some midpoint on the signal line 33 which prevents the DC bias voltage of the DC bias voltage generation section 37 from applying to the transmission signal generation section 36 and the amplifier 40. A control section 39 controls operations of the transmission signal generation section 36 and the reception processing section 41 and the like according to the ultrasound endoscope 3 or ultrasound probe unit 2 connected to the observation apparatus 6.

The present embodiment may also adopt a configuration in which the transmission signal generation section 36, the DC bias voltage generation section 37, the reception processing section 41 and the like of the observation apparatus 6 are used in common between the C-MUTs 9 and 10 or two sets of the transmission signal generation section 36 and the like may be provided in correspondence with the ultrasound endoscope 3 and the ultrasound probe unit 2.

Figure 3A:
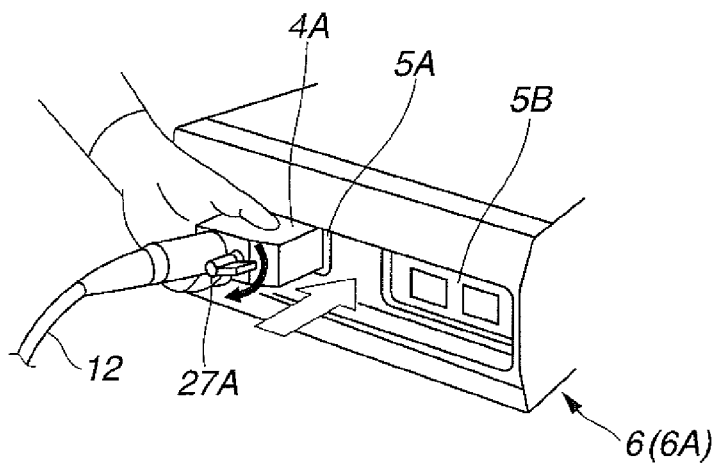
FIG. 3A is a diagram illustrating a case where the connector of the ultrasound probe unit is connected to the connector receiver of the observation apparatus.
Figure 3B:
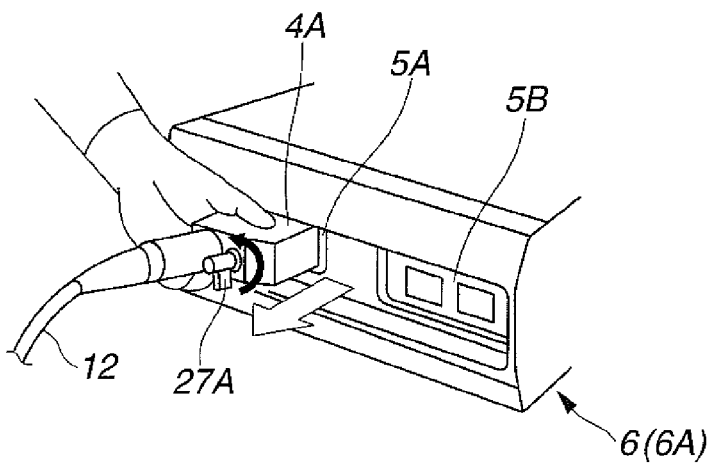
FIG. 3B is a diagram illustrating a case where the connector of the ultrasound probe unit is disconnected from the connector receiver of the observation apparatus.

FIG. 3A and FIG. 3B illustrate how the operator connects or disconnects the connector 4A of the ultrasound probe unit 2 to/from the observation apparatus 6. As shown in FIG. 3A, when mounting (connecting) the connector 4A of the ultrasound probe unit 2 on (to) the observation apparatus 6, the operator inserts the connector 4A on (the connector receiver 5A of) the observation apparatus 6 side as shown by a blank arrow.

After the insertion, the operator turns the lever 27A as shown by an arrow. The turning of the lever 27A changes the state of the connection contact 29 of the connector 4A which is not connected to the connection contact 32 of the connector receiver 5A to a predetermined mounting state in which the connection contact 29 is connected to the connection contact 32.

Furthermore, when unmounting the connector 4A of the ultrasound probe unit 2 mounted on the connector receiver 5A of the observation apparatus 6, the operator performs an operation opposite to that in FIG. 3A as shown in FIG. 3B. That is, as shown in FIG. 3B, the operator turns the lever 27A in a direction opposite to that in FIG. 3A. This turning operation unlocks the mounting state and also causes the connection contact 29 of the aforementioned connector 4A to change the state in which the connection contact 29 is connected to the connection contact 32 of the connector receiver 5A to a state in which the connection contact 29 is not connected and is ready to be disconnected (also referred to as "released state").

After that, the operator pulls out the connector 4A from (the connector receiver 5A of) the observation apparatus 6 side as shown by a blank arrow, and can thereby disconnect the connector 4A from the connector receiver 5A of the observation apparatus 6. Thus, the connector 4A and the connector receiver 5A making up the connection section of the present embodiment are provided with a lock mechanism that keeps a locked state of preventing or regulating disconnection of the connector 4A from the connector receiver 5A (due to careless disconnection operation) in a predetermined mounting state and releases the locked state in a released state set by the turning operation of the lever 27A. The following connector 4B and connector receiver 5B are likewise provided with the lock mechanism.

Figure 4A:
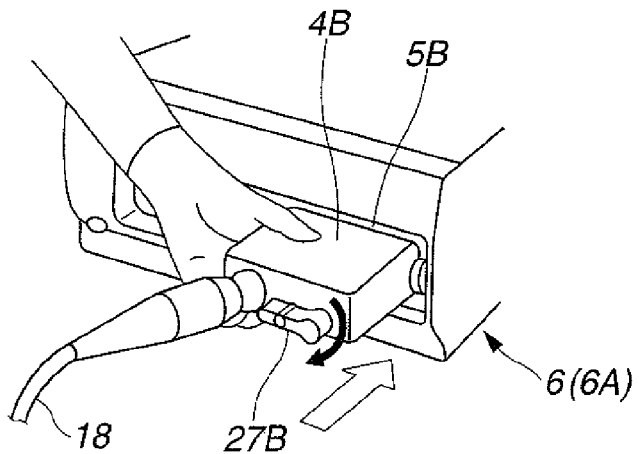
FIG. 4A is a diagram illustrating a case where the connector of the ultrasound endoscope is connected to the connector receiver of the observation apparatus.
Figure 4B:
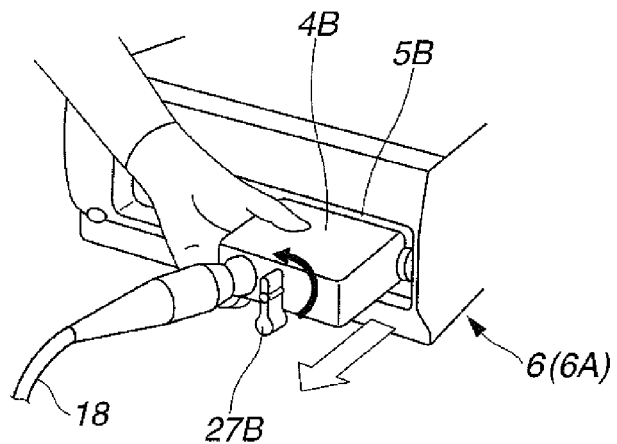
FIG. 4B is a diagram illustrating a case where the connector of the ultrasound endoscope is disconnected from the connector receiver of the observation apparatus.

Furthermore, FIG. 4A and FIG. 4B are diagrams illustrating a case where the connector 4B of the ultrasound endoscope 3 is connected or disconnected to/from the connector receiver 5B of the observation apparatus 6, that is, a case where the connector 4B is attached/detached. As is clear from a comparison with FIG. 3A and FIG. 3B, the attachment/detachment operation is the same as the attachment/detachment operation of the connector 4A of the ultrasound probe unit 2 to/from the connector receiver 5A of the observation apparatus 6 and the operation thereof is also the same.

Figure 5:
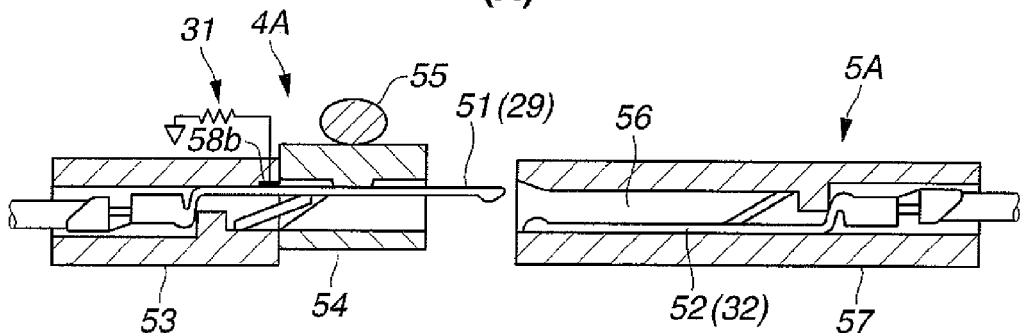
FIG. 5 is a diagram illustrating a schematic configuration when the connection pin of the connector of the ultrasound probe is connected to the connection pin of the connector receiver through a lever operation.
Figure 5:
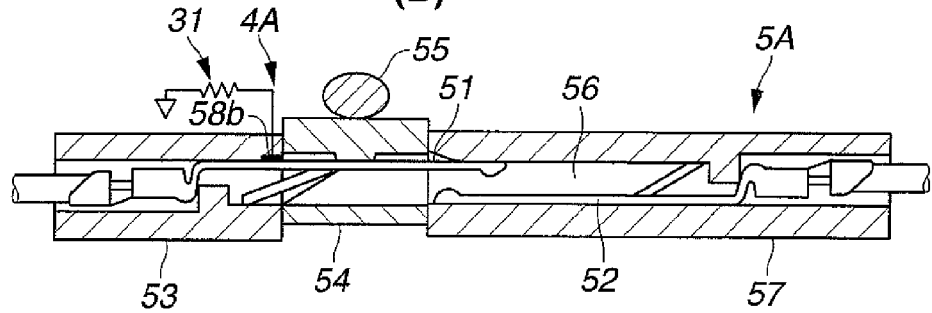
Figure 5:
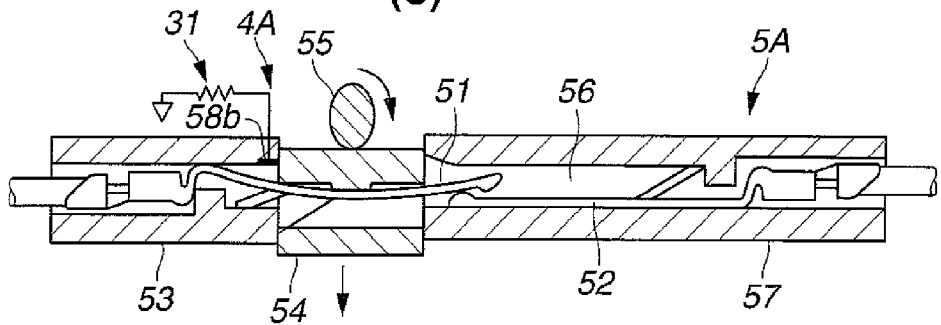

FIG. 5 illustrates a structure example in which the operation of the aforementioned lever 27A causes a contact pin 51 as the connection contact 29 of the connector 4A to be attached/detached to/from a contact pin 52 as the connection contact 32 in the connector receiver 5A of the observation apparatus 6.

FIG. 5(A) shows an unconnected state in which the contact pin 51 of the connector 4A is separate from the contact pin 52 of the connector receiver 5A, FIG. 5(B) shows a state in which although the connector 4A is inserted into and connected to the connector receiver 5A, the contact pin 51 is not connected to the contact pin 52 and FIG. 5(C) shows a predetermined mounting state in which the lever 27A in the state of FIG. 5(B) is turned and the contact pin 51 is connected to the contact pin 52 and locked.

As shown in FIG. 5(A) or the like, the connector 4A has a housing 53 that accommodates the proximal end side of the contact pin 51 and a contact pin holding frame (hereinafter, simply abbreviated as "holding frame") 54 provided at a distal end of the housing 53, in which a substantially central portion in a longitudinal direction of the contact pin 51 is inserted and from which the distal end side of the contact pin 51 protrudes.

The holding frame 54 is moved by a rotating ellipsoidal cam 55 in the direction (vertical direction in FIG. 5) orthogonal to the longitudinal direction of the contact pin 51 (horizontal direction in FIG. 5) in conjunction with the turning operation of the lever 27A.

On the other hand, the connector receiver 5A has a housing 57 that includes a concave section 56 having an opening into which the contact pin 51 is inserted and accommodates the contact pin 52 which is electrically connected to the distal end of the contact pin 51 through contact therewith along the bottom of the concave section 56. When the contact pin 51 is inserted into the connector receiver 5A as shown in FIG. 5(B), the contact pin 51 is inserted along the top surface of the concave section 56, and in this state, the contact pin 51 is set so as not to contact (separate from) the contact pin 52 disposed along the bottom surface of the concave section 56.

Furthermore, in the state of FIG. 5(B), when the lever 27A is turned to cause the cam 55 to rotate 90° as shown in FIG. 5(C), an outer circumferential portion in the major axis direction of the cam 55 causes the holding frame 54 to move downward.

The movement of the holding frame 54 causes the central portion of the contact pin 51 to be pressed downward by a convex section provided on an inner surface of the holding frame 54. Since the proximal end side of the contact pin 51 is regulated, the contact pin 51 closer to the distal end side than the proximal end is deformed while moving downward, and in that case, the distal end of the contact pin 51 moves downward and comes into contact with the contact pin 52.

Furthermore, as described above, the state in FIG. 5(C) is a predetermined mounting state in which the contact pins 51 and 52 remain in contact with each other, and the state in which contact pin 51 is in contact with the contact pin 52 is kept and a locked state is in place in which even if the operator attempts to pull out the connector 4A from the connector receiver 5A, the connector 4A cannot be disconnected.

Figure 6:
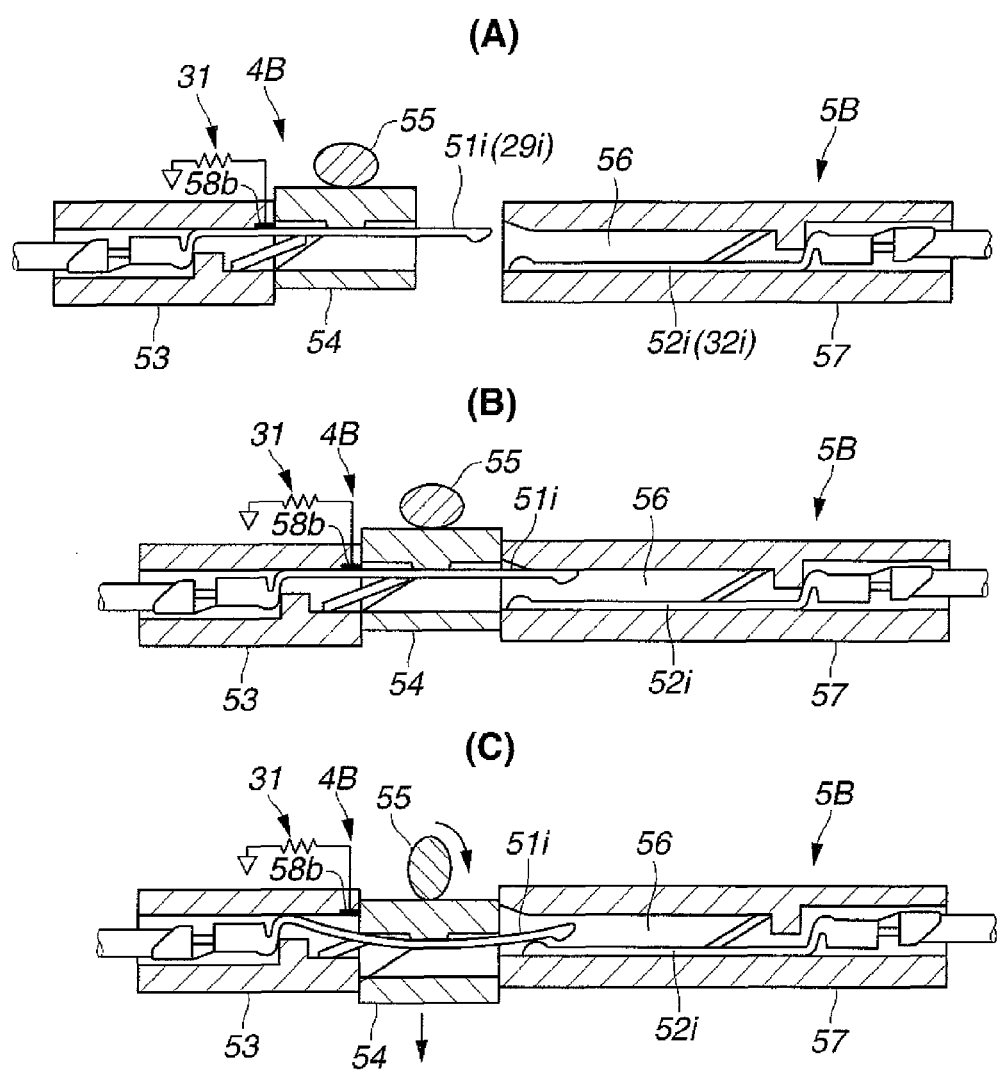
FIG. 6 is a diagram illustrating a schematic configuration when the connection pin of the connector of the ultrasound endoscope is connected to the connection pin of the connector receiver through a lever operation.

On the other hand, in the case of the connector 4B of the ultrasound endoscope 3 and the connector receiver 5B, there are as many configurations shown in FIG. 5 as the number of connection contacts 29$i$ and 32$i$ (that is, connection contacts 29$a$ to 29$n$) and one of such configurations is as shown in FIG. 6.

The configuration shown in FIG. 6 is similar to the case where the connection contacts 29 and 32 shown in FIG. 5(A) are replaced by one set of connection contacts 29$i$ and 32$i$. With such replacement, the contact pins 51 and 52 in FIG. 5 have a structure in which these are replaced by one set of contact pins 51$i$ and 52$i$ as shown in FIG. 6.

In the case of the connector 4B and the connector receiver 5B, there are a plurality of sets of the contact pins 51$i$ and 52$i$ having the structure (shown by the surface of the sheet of FIG. 6) in the direction perpendicular to the surface of the sheet of FIG. 6 and a plurality of sets of the connection contacts 29$i$ and 32$i$ are changed as shown in FIG. 6 together with the cam 55 that rotates in conjunction with the turning operation of the lever 27B.

The connector structure itself described with reference to FIG. 5 and FIG. 6 in which the contact pins 51 (51$i$) and 52 (52$i$) are detachably connected is a publicly known technique.

With such a structure, the present embodiment changes the destination of the common contact c of the switches 25 and 25i from the contact a to the contact b or from the contact b to the contact a using the cam 55 or the like making up the connection section 26 in conjunction with the turning operation of the levers 27A and 27B described in FIG. 2A and FIG. 2B.

For this reason, in the present embodiment, the connection contact 29 (contact pin 51 in FIG. 5) in FIG. 2A forms the common contact c of the switch 25 (see FIG. 6), and as shown in FIG. 5, a contact member 58b having the function of the contact b of the switch 25 is provided, for example, at a position near the opening in the upper part of the inner surface of the housing 53.

The contact member 58b is electrically connected to the discharge section 31 via the signal line 30 as shown in FIG. 5 and FIG. 2A. Furthermore, the contact pin 52 (connection contact 32 in FIG. 2A) shown in FIG. 5 is provided with the function of the contact a as the connector receiver 5A.

Therefore, the electrical connection structure in the present embodiment corresponding to FIG. 5(A) to FIG. 5(C) is as shown in FIG. 7(A) to FIG. 7(C). FIG. 7(A) corresponds to FIG. 5(A) and shows the contact pin 51 having the function of the connection contact 29 and the common contact c and the contact pin 51 is not connected to the connection contact 32 and the contact pin 52 that makes up the contact a.

In this state, the signal line 24 connected to the lower electrode 22 is electrically connected to the discharge section 31 via the contact member 58b that contacts the contact pin 51 (having the function of the contact b).

In the state of FIG. 7(B) corresponding to FIG. 5(B), the contact pin 51 is set at a position above the contact pin 52. Furthermore, the contact pin 51 in this state is in the same electric connection state as in FIG. 7(A).

When the lever 27A is turned in the state of FIG. 5(B), a state in FIG. 5(C) is set, and in the state in FIG. 7(C) corresponding to FIG. 5(C), the contact pin 51 moves downward, detached from the contact member 58b, the distal end of the contact pin 51 comes into contact with the contact pin 52 and is thereby electrically connected.

In the case of the ultrasound endoscope 3, a contact member 58b is provided as shown in FIG. 6 (as in the case of FIG. 5) and the contact member 58b is electrically connected to the discharge section 31 via the signal line 30i as shown in FIG. 6 and FIG. 2B.

Figure 7:
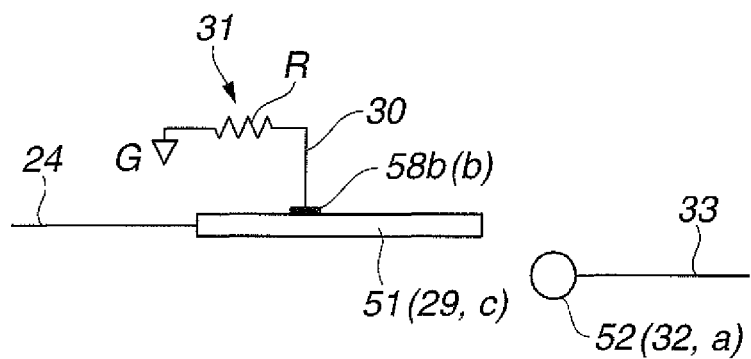
FIG. 7 is a schematic diagram illustrating a case where a switch is changed in conjunction with an operation of connecting the connection pin of the connector of the ultrasound probe unit to the connection pin of the connector receiver through a lever operation in correspondence with FIG. 5.
Figure 7:
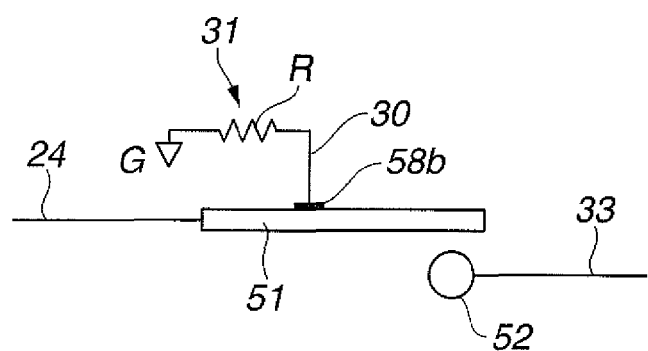
Figure 7:
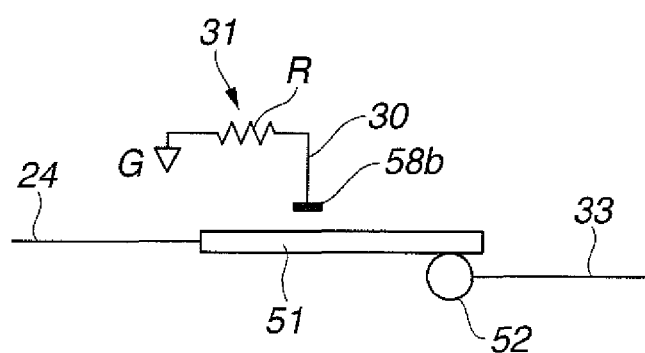
Figure 8:
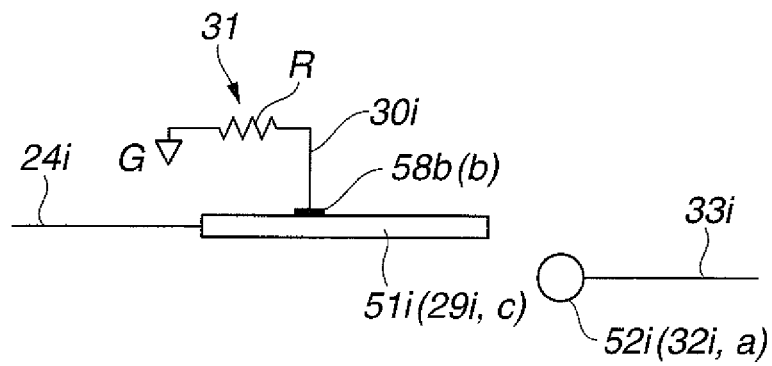
FIG. 8 is a schematic diagram illustrating a case where a switch is changed in conjunction with an operation of connecting the connection pin of the connector of the ultrasound endoscope to the connection pin of the connector receiver through a lever operation in correspondence with FIG. 6.
Figure 8:
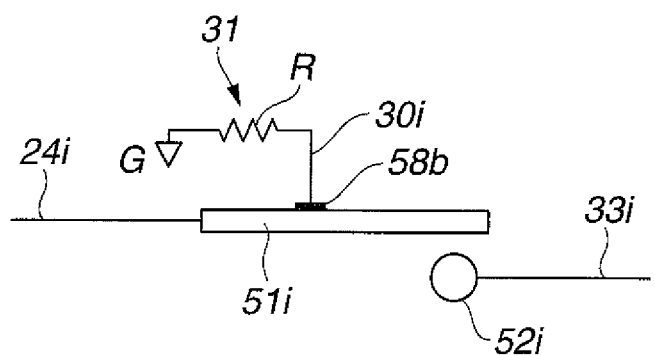
Figure 8:
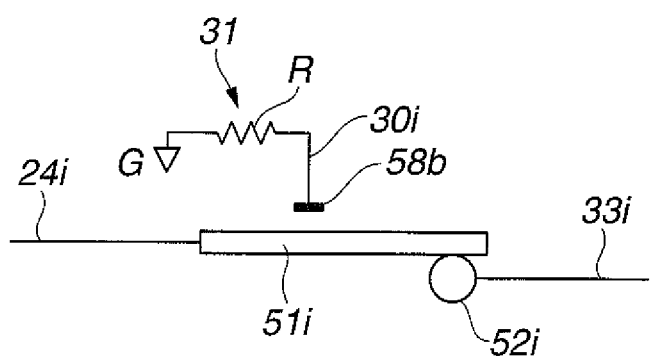

In correspondence with FIG. 7 corresponding to FIG. 5 in the case of the ultrasound probe unit 2, the diagram corresponding to FIG. 6 in the case of the ultrasound endoscope 3 is as shown in FIG. 8. By renaming components in FIG. 8 corresponding to those in FIG. 5 and FIG. 6 (e.g., reading reference numeral 29 as 29i, 30 as 30i, 32 as 32i, 33 as 33i, 51 as 51i and 52 as 52i), both operations become similar, and so descriptions thereof will be omitted.

As described above, although a difference between mechanical scan and electronic scan exists between the configuration of the ultrasound probe unit 2 and the observation apparatus 6 corresponding to the ultrasound probe unit 2 that transmits/receives ultrasound and the configuration of the ultrasound endoscope 3 and the observation apparatus 6 corresponding to the ultrasound endoscope 3 that transmits/receives ultrasound, these configurations are the same in the sense that they have principal features in the present embodiment.

For this reason, descriptions of the case corresponding to the ultrasound endoscope 3 will be omitted.

Thus, in the present embodiment, when the ultrasound probe unit 2 or ultrasound endoscope 3 as the ultrasound device mounted with the C-MUT 10 or 9 and the observation apparatus 6 to which the ultrasound device is detachably attached and which includes a transmission/reception processing system that performs transmission/reception signal processing on the C-MUT 10 or 9 are connected, the common contact c of the switches 25 and 25i is set to be connected to the contact a so that the C-MUT 10 or 9 is connected to the transmission/reception processing system and the DC bias voltage generation section 37.

Furthermore, when the ultrasound device is disconnected from the observation apparatus 6, the ultrasound device cannot be disconnected from the observation apparatus 6 unless the lever 27A or 27B is operated so as to set the common contact c of the switches 25 and 25i to be connected to the contact b of the discharge section 31 side. That is, when the ultrasound device is mounted on the observation apparatus 6 and ready for use, such a structure is provided that the ultrasound device cannot be carelessly disconnected from the observation apparatus 6.

The ultrasound diagnostic system 1 of the present embodiment in such a configuration includes the ultrasound probe unit 2 or the ultrasound device made up of the ultrasound endoscope 3 mounted with the capacitive micromachined ultrasonic transducer (C-MUT 10 or 9), the connector 4A (or 4B) and connector receiver 5A (or 5B) as the connection section for detachably connecting the ultrasound device and the observation apparatus 6 provided with the transmission signal generation section 36 that generates a transmission signal to drive the C-MUT, the discharge section 31 to discharge the charge applied to the C-MUT and the switches 25 and 25i as the switching section arranged on the signal line between the C-MUT and the observation apparatus 6.

When the ultrasound device is set to a predetermined mounting state with respect to the observation apparatus 6 according to the attachment/detachment state of the connection section between the ultrasound device and the observation apparatus 6, the C-MUT is electrically connected to the transmission signal generation section 36 via the signal line and when the ultrasound device is disconnected from the observation apparatus 6, switching of the switches 25 and 25i is performed so that the charge of the C-MUT is discharged by the discharge section 31.

Operation of the present embodiment having such a configuration will be described.

When the ultrasound probe unit 2 is used connected to the observation apparatus 6 to perform an ultrasound inspection, as shown in FIG. 3A, the connector 4A is inserted so as to engage with the connector receiver 5A, and then the lever 27A is turned to set a predetermined mounting state.

The common contact c of the switch 25 is electrically connected to the contact a (from the contact b via the contact member 58a) so that the signal line 24 connected to the lower electrode 22 of the C-MUT 10 is connected to the contact pin 52 (connection contact 32) of the observation apparatus 6 as shown in FIG. 7(C).

Therefore, the C-MUT 10 of the ultrasound probe unit 2 can be driven by the observation apparatus 6. The operator sets the DC bias voltage generation section 37 so as to output a DC bias voltage suitable for driving the C-MUT 10.

Through the signal line 33 or the like, a transmission signal from the transmission signal generation section 36 is superimposed on the DC bias voltage and outputted to the ultrasound probe unit 2 side. As shown in FIG. 2A, since the common contact c is electrically connected to the contact a, the DC bias voltage on which the transmission signal is superimposed is applied to the lower electrode 22 of the C-MUT 10 and the mechanically scanned C-MUT 10 transmits ultrasound to the subject side.

Ultrasound reflected by a portion of the subject where an acoustic impedance is changing is received by the C-MUT 10 and becomes an echo signal.

The echo signal superimposed on the DC bias voltage passes through the switch 25, whose DC bias voltage is cut by the capacitor 42 and the signal is then amplified by the amplifier 40.

The echo signal amplified by the amplifier 40 is subjected to signal processing by the reception processing section 41, converted to a video signal, outputted to the monitor 6B and an ultrasound tomographic image is displayed on the display screen of the monitor 6B.

After the ultrasound inspection using ultrasound, the operator turns OFF the power to the observation apparatus 6 to stop the function of transmitting/receiving ultrasound (and the function of generating a DC bias voltage).

When the ultrasound probe unit 2 is disconnected from the observation apparatus 6, the lever 27A is turned as shown in FIG. 3B and it is thereby possible to disconnect the connector 4A of the ultrasound probe unit 2 from the connector receiver 5A of the observation apparatus 6.

In conjunction with the turning of the lever 27A at this time, the common contact c of the switch 25 is connected to the contact b, that is, the resistor R making up the discharge section 31. As a result, the charge of the C-MUT 10 is discharged to ground via the resistor R of the discharge section 31 shown in FIG. 2A. This makes it possible to eliminate the charge present in the C-MUT 10.

Therefore, according to the present embodiment, when the ultrasound probe unit 2 as the ultrasound device mounted with the C-MUT 10 as the capacitive micromachined ultrasonic transducer is disconnected from the observation apparatus 6, it is possible to discharge and eliminate the charge so that the charge of the C-MUT 10 is not accumulated.

Furthermore, according to the present embodiment, (since the charge present in the C-MUT 10 can be eliminated as described above), it is possible to reliably eliminate the possibility that the charge present in the C-MUT 10 may cause discharge when the connector 4A is disconnected from the connector receiver 5A causing deterioration of the contact (contact pin) or a high voltage at the time of discharge may damage the transmission/reception processing system that performs transmission/reception in the observation apparatus 6.

Furthermore, according to the present embodiment, it is also possible to reduce or prevent the advance of deterioration of the C-MUT 10 itself due to the charge accumulated in the capacitive micromachined ultrasonic transducer (C-MUT) 10 for a long time. Moreover, by preventing charge from being accumulated in the C-MUT 10, it is possible to ensure stable sensitivity for a long period of time. In addition, it is possible to realize an ultrasound diagnostic system 1 with a high degree of reproducibility.

Furthermore, according to the present embodiment, when the connector 4A and the connector receiver 5A are connected and the lever 27A is set to a lock position, the connector 4A cannot be disconnected from the connector receiver 5A, and it is thereby possible to reliably prevent the ultrasound probe unit 2 from being carelessly disconnected from the observation apparatus 6 during an ultrasound inspection. The present embodiment can provide the ultrasound diagnostic system 1 with a high degree of operability and reliability.

Furthermore, operation when the ultrasound endoscope 3 is detachably connected to the observation apparatus 6 also has similar operation and effects. In this case, by reading the C-MUT 10 as C-MUT 9 or C-MUT element 9$i$, switch 25 as 25$i$, lever 27A as lever 27B, connector 4A as connector 4B, connector receiver 5A as connector receiver 5B, similar operation and effects can be obtained.

For example, as shown in FIG. 4A, when the connector 4B of the ultrasound endoscope 3 is attached to the connector receiver 5B of the observation apparatus 6, the operator inserts the connector 4A on (the connector receiver 5B of) the observation apparatus 6 side as shown by a blank arrow.

After the insertion, the operator turns the lever 27B as shown by the arrow. When the lever 27B is turned, as shown in FIG. 8(A) and FIG. 8(B), the signal line 24$i$ (connected to the lower electrode 22$i$ of each C-MUT element 9$i$ making up the C-MUT 9) connected to the contact b is changed to a state in which it is connected to the contact pin 52$i$ (connection contact 32$i$) of the observation apparatus 6.

It is then possible to set a state in which the observation apparatus 6 can transmit/receive ultrasound to/from the C-MUT 9 of the ultrasound endoscope 3.

Furthermore, when the connector 4B of the ultrasound endoscope 3 connected to the connector receiver 5B of the observation apparatus 6 is disconnected, as shown in FIG. 4B, operation opposite to that in FIG. 4A is performed. That is, as shown in FIG. 4B, the operator turns the lever 27B in the direction opposite to that in FIG. 4A.

With this turning operation, the mounting state is unlocked and the signal line 24$i$ connected to the lower electrode 22$i$ of each C-MUT element 9$i$ making up the C-MUT 9 is changed to a state in which it is connected to the contact b. In this state, it is possible to discharge the charge accumulated in the electrode of each C-MUT element to ground through the discharge section 31.

Furthermore, the operator performs operation of separating the connector 4B from (the connector receiver 5B of) the observation apparatus 6 side, and can thereby disconnect the connector 4B from the connector receiver 5B of the observation apparatus 6. The present embodiment provides effects similar to those in the case of the aforementioned ultrasound probe unit 2.

In FIG. 2A and FIG. 2B, the resistor R is used as the discharge section 31, but other devices such as a diode may also be used.

A configuration has been described above where the contacts a and b of the switches 25 and 25$i$ are changed in conjunction with the turning operation of the lever 27A or 27B, but the present invention is not limited to the structure in which the ultrasound device and the observation apparatus 6 are detachably connected through the turning operation of the lever 27A or 27B. For example, the lever 27A or 27B may be moved sliding to change the contact of the switches 25 and 25$i$.

In the above configuration, the observation apparatus 6 is provided with the connection section to detachably connect both mechanical scan and electronic scan ultrasound devices, but the present invention is not limited to such a configuration and it is obvious that the present invention is also applicable to an observation apparatus in which any one of those scan ultrasound devices is detachably connected to the ultrasound device.

Second Embodiment

The configuration shown in FIG. 2A and FIG. 2B has been described as a configuration in which a DC bias voltage and a transmission signal are applied to the lower electrodes 22 and 22$i$ of the C-MUT 10 or 9. By contrast, a configuration may also be adopted in which, for example, a transmission/reception signal is applied to the upper electrode 21$i$ side of each C-MUT element 9$i$ making up the C-MUT 9 and a DC bias voltage is applied to the lower electrode 22$i$ side.

Figure 9:
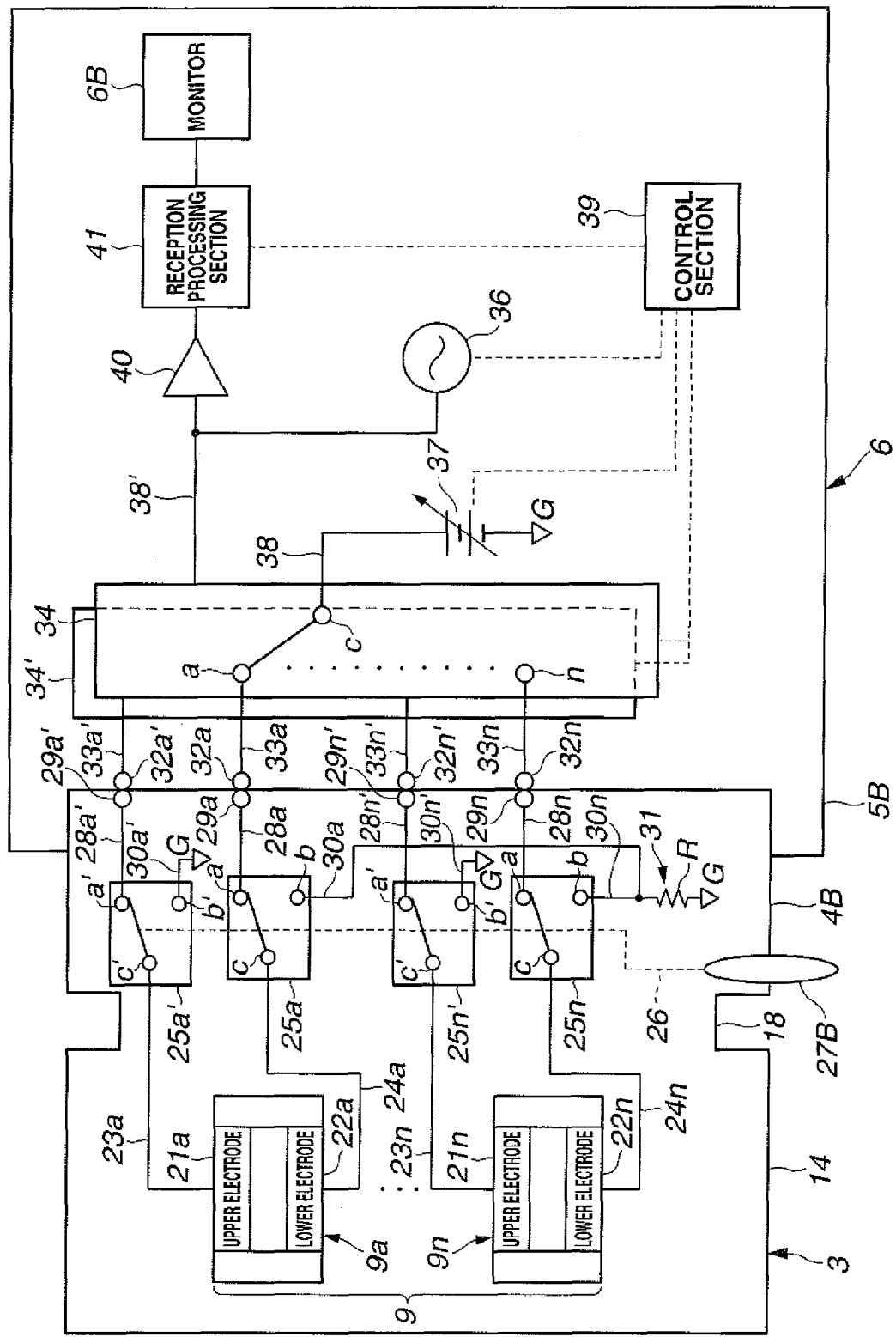
FIG. 9 is a configuration diagram illustrating a configuration of an ultrasound endoscope and an observation apparatus according to a second embodiment of the present invention.

FIG. 9 shows a configuration of an ultrasound endoscope 3 and an observation apparatus 6 in an ultrasound diagnostic system according to a second embodiment of the present invention corresponding to this case. In the configuration shown in FIG. 9, switches 25$i$ and 25$i'$ that form a pair (instead of the switch 25$i$ in FIG. 2B) are provided via a connection section 26 connected to a lever 27B in the configuration of FIG. 2B.

A common contact c of the switch 25$i$ is connected to a lower electrode 22$i$ via a signal line 24$i$ and a common contact c' of the switch 25$i'$ is connected to the upper electrode 21$i$ via a signal line 23$i$.

Furthermore, a contact b of the switch 25$i$ is connected to a ground via a resistor R of a discharge section 31 via a signal line 30$i$ and a contact b' of the switch 25$i'$ is connected to the ground via a signal line 30$i'$. Furthermore, a contact a of the switch 25$i$ and a contact a' of the switch 25$i'$ are connected to connection contacts 29$i$ and 29$i'$ of a connector 4A via signal lines 28$i$ and 28$i'$ respectively.

Furthermore, a connection contact 32$i$ of a connector receiver 5B connected to a connection contact 29$i$ of the connector 4A is connected to a DC bias voltage generation section 37 via a signal line 33$i$, a multiplexer 34 and a signal line 38.

Furthermore, a connection contact 32$i'$ of the connector receiver 5B connected to the connection contact 29$i'$ of a connector 4B is connected to a transmission signal generation section 36 and an input end of an amplifier 40 via the signal line 33$i'$, a multiplexer 34' and a signal line 38'. Switching of the multiplexers 34 and 34' is controlled by a control section 39.

The present embodiment adopts a configuration with no capacitor 42 in FIG. 2B.

The lever 27B, the connection section 26 and the switches 25$i$ and 25$i'$ of the present embodiment shown in FIG. 9 can be formed in a configuration similar to that shown, for example, in FIG. 6 and FIG. 8.

That is, a configuration similar to that of the connection contacts 29$i$ and 32$i$ described in FIG. 6 and FIG. 8 may also be applied to the connection contacts 29$i'$ and 32$i'$ added from the connection contacts 29$i$ and 32$i$ of the first embodiment.

As described in the first embodiment, when the mounting state is set in which the lever 27B is locked as shown in FIG. 6(C), the common contacts c and c' of the switches 25$i$ and 25$i'$ are connected to the contacts a and a' respectively. That is, also in the present embodiment, in a predetermined mounting state in which the ultrasound endoscope 3 is connected to the observation apparatus 6, the common contacts c and c' of the switches 25$i$ and 25$i'$ are connected to the contacts a and a' as shown in FIG. 9.

In this state, the upper electrode 21$i$ of each C-MUT element 9$i$ making up the C-MUT 9 is connected to the transmission/reception signal system of the observation apparatus 6 via the switch 25$i'$. Furthermore, the lower electrode 22$i$ of each C-MUT element 9$i$ is connected to the DC bias voltage generation section 37 of the observation apparatus 6 via the switch 25$i$.

Applying a transmission signal and a DC bias voltage from the observation apparatus 6 to the C-MUT element 9$i$ allows ultrasound to be outputted from each C-MUT element 9$i$. Furthermore, an ultrasound tomographic image is displayed on the monitor 6B by performing signal processing on the echo signal received through each C-MUT element 9$i$.

When the ultrasound inspection ends, the ultrasound endoscope 3 can be disconnected from the observation apparatus 6 by turning the lever 27B and setting the connector 4B at a position where it can be disconnected from the connector receiver 5B (released position where the connection can be released) as in the case described in the first embodiment.

When the lever 27B is turned and the released position where the connection can be released is set, that is, when a state corresponding to that in FIG. 6(B) is set, the common contacts c and c' of the switches 25$i$ and 25$i'$ are connected to the contacts b and b' respectively and the charge of each C-MUT element 9$i$ is discharged to ground.

Furthermore, even when the connector 4B is disconnected from the connector receiver 5B in the state in FIG. 6(B) and set in the unconnected state in FIG. 6(A), the connection state of the switches 25$i$ and 25$i'$ in FIG. 6(B) is maintained.

Therefore, although the present embodiment adopts a configuration in which the switch 25$i$ of the first embodiment is modified into a pair of the switches 25$i$ and 25$i'$, the present embodiment has substantially the same operations as those of the first embodiment. Moreover, the present embodiment has effects similar to those of the first embodiment.

In FIG. 9, a case with the electronic scan ultrasound endoscope 3 has been described, but it is obvious that the present invention is also applicable to a case with a mechanical scan ultrasound probe unit 2. That is, one of the plurality of C-MUT elements 9$i$ making up the C-MUT 9 in FIG. 9 is replaced with the C-MUT 10, and similar operation and effects can be obtained in this case, too.

In FIG. 9, since charge may be accumulated also on the upper electrode 21$i$ side, a configuration may also be adopted in which the contact b' of the switch 25$i'$ in FIG. 9 is connected to the ground via a discharge device that discharges the charge. In this configuration, the signal line 23$i$ connected to the upper electrode 21$i$ is changed to the signal line 28$i'$ side of the contact a' and the discharge device side of the contact b' through the switching by the switch 25$i'$ in conjunction with the operation of the lever 27B.

Thus, when the signal line 23$i$ is switched so as to be electrically continuous with the discharge device side through the operation of the lever 27B, it is possible to discharge the charge of the upper electrode 21$i$ also on the upper electrode 21$i$ side as in the case of the lower electrode 22$i$ side.

Third Embodiment

Next, a third embodiment of the present invention will be described. When the connection between the ultrasound probe unit 2 or ultrasound endoscope 3 and the observation apparatus 6 is released (disconnected) through the structure using the aforementioned levers 27A and 27B, it is preferable to set a state in which the discharge section 31 is electrically connected to the C-MUT 10 or 9 before the connection contact 29 of the connector 4A of the ultrasound probe unit 2 or the connection contact 29$i$ (29$i$) of the ultrasound endoscope 3 is separated from the connection contact 32 or 32$i$ (32$i$) of the connector receiver 5A or 5B of the observation apparatus 6 through the disconnection.

Figure 10:
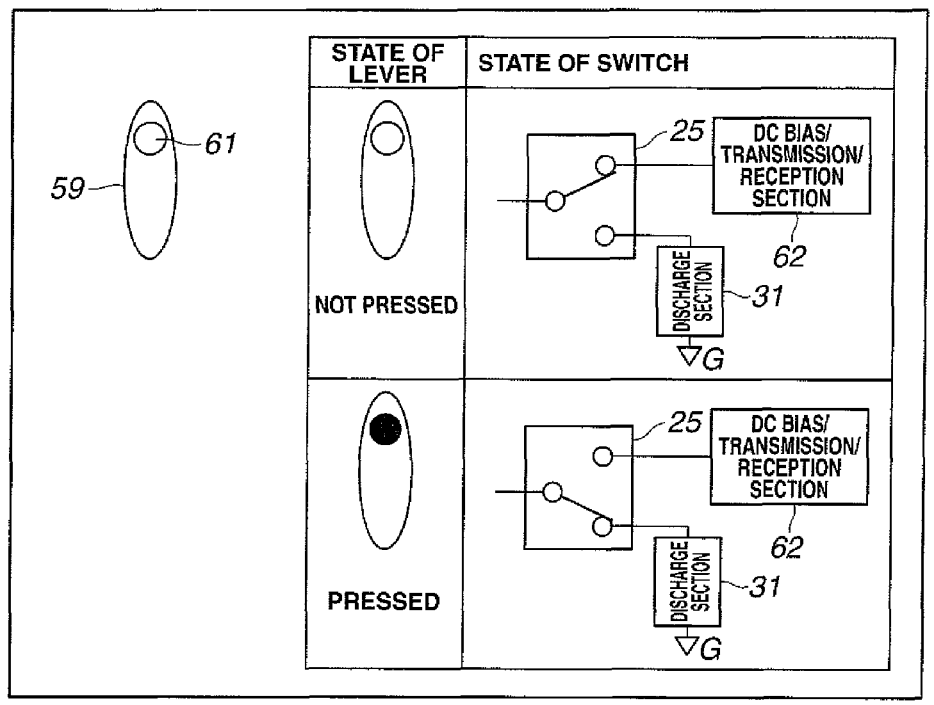
FIG. 10 is a diagram illustrating in a table form the status of a button for switching a contact point of the switch provided in the lever and contents of the switching state of the switch according to a third embodiment of the present invention.

The aforementioned first and second embodiments are configured to realize this and another configuration example for realizing this is shown using a table in FIG. 10. FIG. 10 shows a lever 59 provided with a button 61 to change the switch 25 (25$i$ in the case of the ultrasound endoscope 3) of the ultrasound probe unit 2 and a state in which the button is pressed determines whether the turning of the lever 59 is regulated or not.

As shown on the left side of the table in FIG. 10, a white circle represents a state of the button 61 in which the button 61 is not pressed and a black circle represents a state of the button 61 in which the button 61 is pressed.

When the button 61 is not pressed as shown on the right side of FIG. 10, the switch 25 is connected to a DC bias/transmission/reception section 62 on the observation apparatus 6 side.

Here, the DC bias/transmission/reception section 62 represents the DC bias voltage generation section 37 connected to the signal line 33, the transmission signal generation section 36 connected via the capacitor 42, the amplifier 40 and the reception processing section 41 in FIG. 2A.

On the other hand, in the case of the ultrasound endoscope 3, the DC bias/transmission/reception section 62 represents the multiplexer 34 connected to the signal line 33i, the DC bias voltage generation section 37, the transmission signal generation section 36 connected via the capacitor 42, the amplifier 40 and the reception processing section 41 in FIG. 2B.

On the other hand, when the button 61 is pressed, the switch 25 is connected to the discharge section 31 side. A structure is adopted for the lever 59 in such a configuration in which the lever 59 cannot be turned unless the button 61 is pressed (state shown by the black circle in FIG. 10) and the ultrasound probe unit 2 cannot be disconnected from the observation apparatus 6 unless the lever 59 is turned.

When such a configuration is adopted, for the connection between the ultrasound probe unit 2 and the observation apparatus 6, turning the lever before the disconnection causes the C-MUT 10 to be electrically connected to the discharge section 31.

Figure 11:
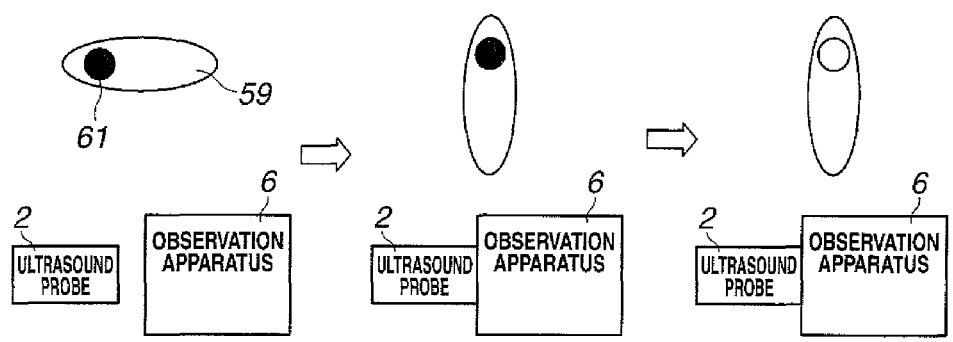
FIG. 11 is a diagram illustrating a state as to whether the button provided on the lever is pressed or not and a connection/disconnection relationship between the ultrasound probe unit and the observation apparatus.

FIG. 11 shows this state. The left figure of FIG. 11 shows a state in which the ultrasound probe unit 2 and the observation apparatus 6 are unconnected. Since the button 61 of the lever 59 is pressed, the switch 25 is connected to the discharge section 31 and the horizontal position of the lever 59 indicates that the ultrasound probe unit 2 is not connected to the observation apparatus 6.

The figure in the middle of FIG. 11 shows a state in which the ultrasound probe unit 2 and the observation apparatus 6 are connected. In this case, the lever 59 is turned to an upright position indicating that the ultrasound probe unit 2 is connected to the observation apparatus 6. However, the switching state of the switch 25 remains as shown in the lower part of FIG. 10.

The right figure of FIG. 11 indicates that the button 61 of the lever 59 is operated to be set (changed) to a state in which the button 61 is not pressed, showing that the ultrasound probe unit 2 is connected to the observation apparatus 6 in a predetermined mounting state and that the switch 25 in FIG. 10 is changed to the DC bias/transmission/reception section 62 side.

The operation for disconnecting the ultrasound probe unit 2 from the observation apparatus 6 is opposite to these operations and by operating the button 61 to cause the switch 25i to be connected to the discharge section 31 (middle of FIG. 11) and then turning the lever 59, the ultrasound probe unit 2 can be disconnected from the observation apparatus 6.

According to the present embodiment, when the ultrasound probe unit 2 is released (disconnected) from the observation apparatus 6, it is possible to get the discharge section 31 connected to the C-MUT 10 before the release. The present embodiment also has effects similar to those of the first embodiment and the second embodiment.

As described in the case with the ultrasound probe unit 2, the present embodiment is likewise applicable to a case with the electronic scan ultrasound endoscope 3 and can obtain similar effects.

Fourth Embodiment

Figure 12:
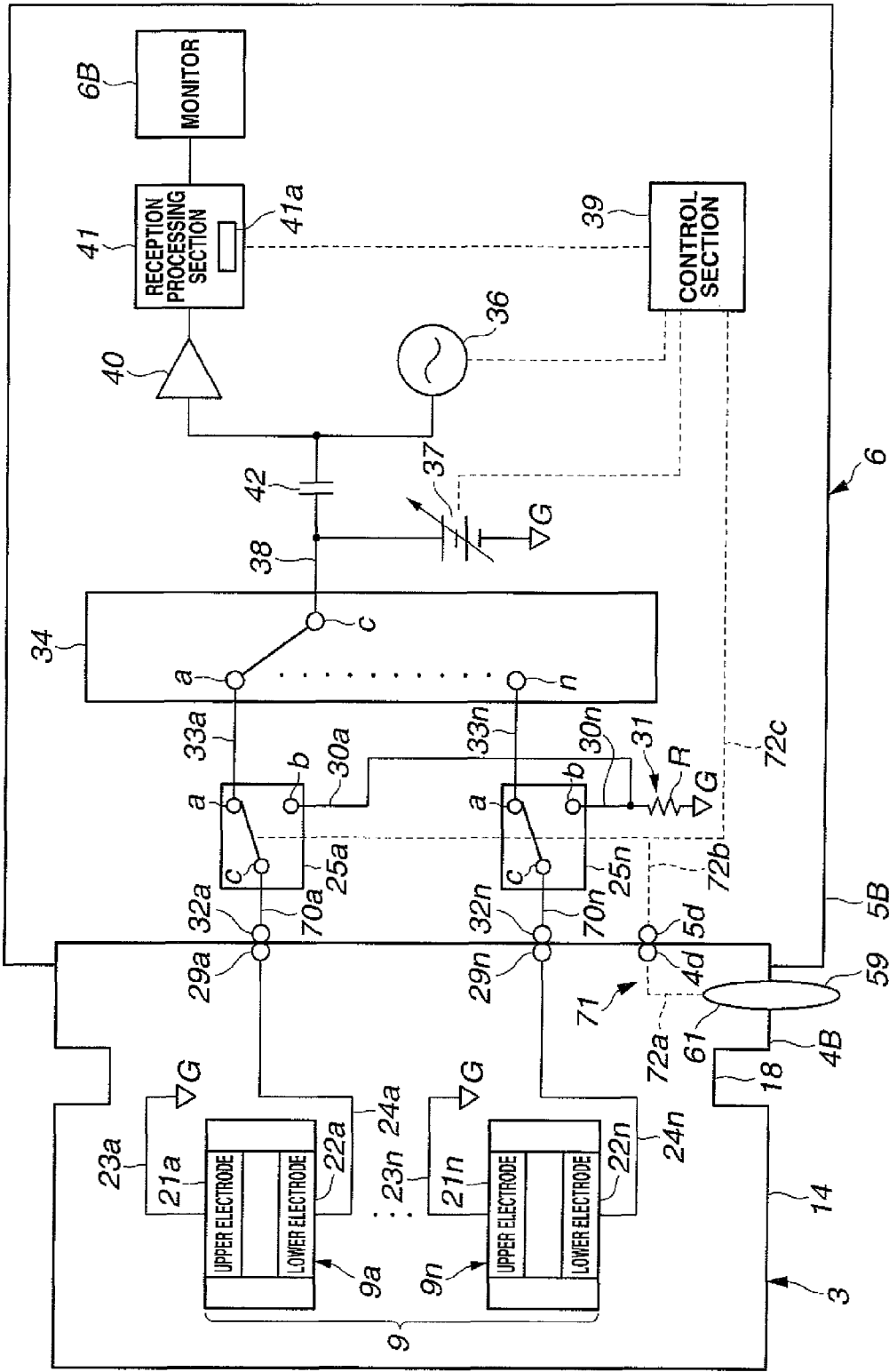
FIG. 12 is a configuration diagram illustrating a configuration of an ultrasound probe unit and an observation apparatus according to a fourth embodiment of the present invention.

In the aforementioned embodiments, the switches 25 and 25i (25i') and the discharge section 31 are present on the ultrasound probe unit 2 or ultrasound endoscope 3 side, but these may be set up on the observation apparatus 6. FIG. 12 illustrates an ultrasound endoscope 3 and an observation apparatus 6 according to a fourth embodiment as such a configuration example.

The present embodiment adopts a lever 59 provided with a button 61 on the ultrasound endoscope 3 side instead of the lever 27B in the configuration of FIG. 2B. Moreover, the switch 25i and the discharge section 31 provided on the ultrasound endoscope 3 side in FIG. 2B are set up on the observation apparatus 6.

As shown in FIG. 12, a signal line 24i connected to a lower electrode 22i is connected to a connection contact 29i, a connection contact 32i is connected to a common contact c of the switch 25i provided inside the observation apparatus 6 via a signal line 70i. Furthermore, a contact a of the switch 25i is connected to a contact i of a multiplexer 34 via a signal line 33i.

Furthermore, a contact b of the switch 25i is connected to the discharge section 31 via a signal line 30i.

Furthermore, in the present embodiment, a transmission section 71 transmits control information for controlling the switch 25i or a control state to the switch 25i from the lever 59.

As a configuration example in this case, ON/OFF by the pressing operation of the button 61 provided in the lever 59 is transmitted to the switch 25i inside the observation apparatus 6 via a signal line 72a, connection contacts 4d and 5d and a signal line 72b that form a transmission section 71.

As shown in FIG. 12, a configuration may also be adopted in which the transmission section 71 is connected to a control section 39 that manages the entire operation of the observation apparatus 6 via a signal line 72c connected to the signal line 72b. That is, the ON/OFF operation of the button 61 in the lever 59 may be transmitted to the control section 39.

In this way, the control section 39 decides whether the button 61 of the lever 59 is pressed or not and sends the decision result to a reception processing section 41. The reception processing section 41 has an information display processing section 41a that generates an information display video signal to display information corresponding to the switching state of the switch 25i according to the decision result.

The reception processing section 41 superimposes the information display video signal on a video signal of an ultrasound tomographic image, outputs the signal to a monitor 6B and the monitor 6B displays the information.

As in the aforementioned case, the control section 39 controls operations of a transmission signal generation section 36, a DC bias voltage generation section 37 and the reception processing section 41. The control section 39 may also perform a switching operation of the switch 25i according to the decision result of the button 61. Alternatively, switching between the contacts of the switch 25i may be directly performed using a signal through the operation of the button 61. Furthermore, the switch 25i may be configured as an electric switch, relay switch or the like.

Figure 13:
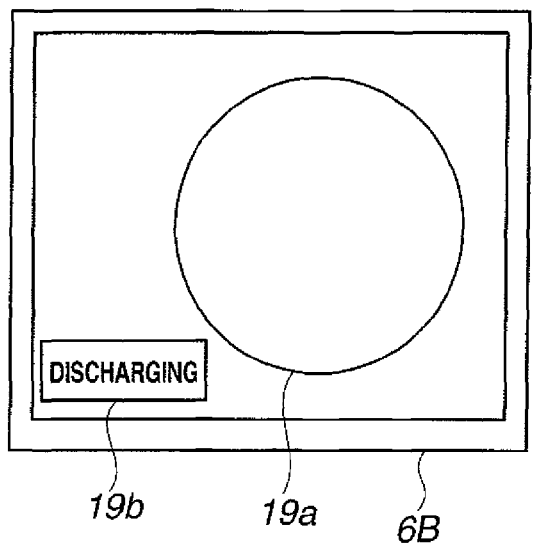
FIG. 13 is a diagram illustrating an example where information of a setting state of the switch or the like is displayed on a monitor according to the fourth embodiment.
Figure 13:
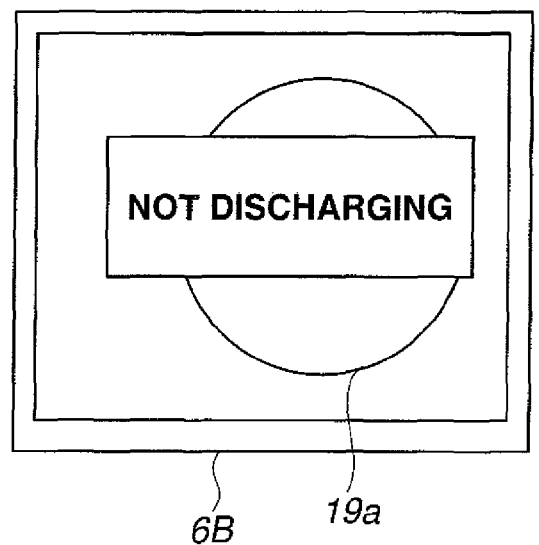

FIG. 13 illustrates a display example of information on the monitor 6B. While the ultrasound endoscope 3 is connected to the observation apparatus 6, for example, an information display area 19*b* of a peripheral section of a display area 19*a* of an ultrasound tomographic image on a screen of the monitor 6B as shown in FIG. 13(A) displays information such as a message "discharging."

This information need not always be displayed but may be displayed according to the display control operation from an operation section (not shown) that operates the observation apparatus 6.

On the other hand, when the ultrasound endoscope 3 is disconnected from the observation apparatus 6, if the operator attempts to disconnect the ultrasound endoscope 3 before discharge, a message "not discharged" may be displayed on the monitor 6B in a large size as shown in FIG. 13(B). After allowing the operator to discharge, a message may be given to the operator to guide the operator to perform a disconnection operation.

Other effects of the present embodiment are substantially the same as those of the aforementioned embodiments.

Although the present embodiment has been described by taking a case of the electronic scan ultrasound endoscope 3, the present embodiment is also applicable to a case of the mechanical scan ultrasound probe unit 2. The present embodiment can obtain operation and effects similar to those of the electronic scan ultrasound endoscope 3.

In the aforementioned embodiments, the ultrasound probe unit 2 may be adapted to an electronic scan configuration. Alternatively, a mechanical scan ultrasound endoscope may be adapted instead of the electronic scan ultrasound endoscope 3. Moreover, the ultrasound probe unit 2 shown in FIG. 1 has a configuration in which the ultrasound probe 13 to be used inserted in the body is detachably attached to the drive unit 11, but a structure may also be adopted in which the ultrasound probe unit 2 is integrated with the drive unit 11. Furthermore, the ultrasound probe unit 2 may also be an ultrasound probe to be used outside the body.

Fifth Embodiment

Figure 14:
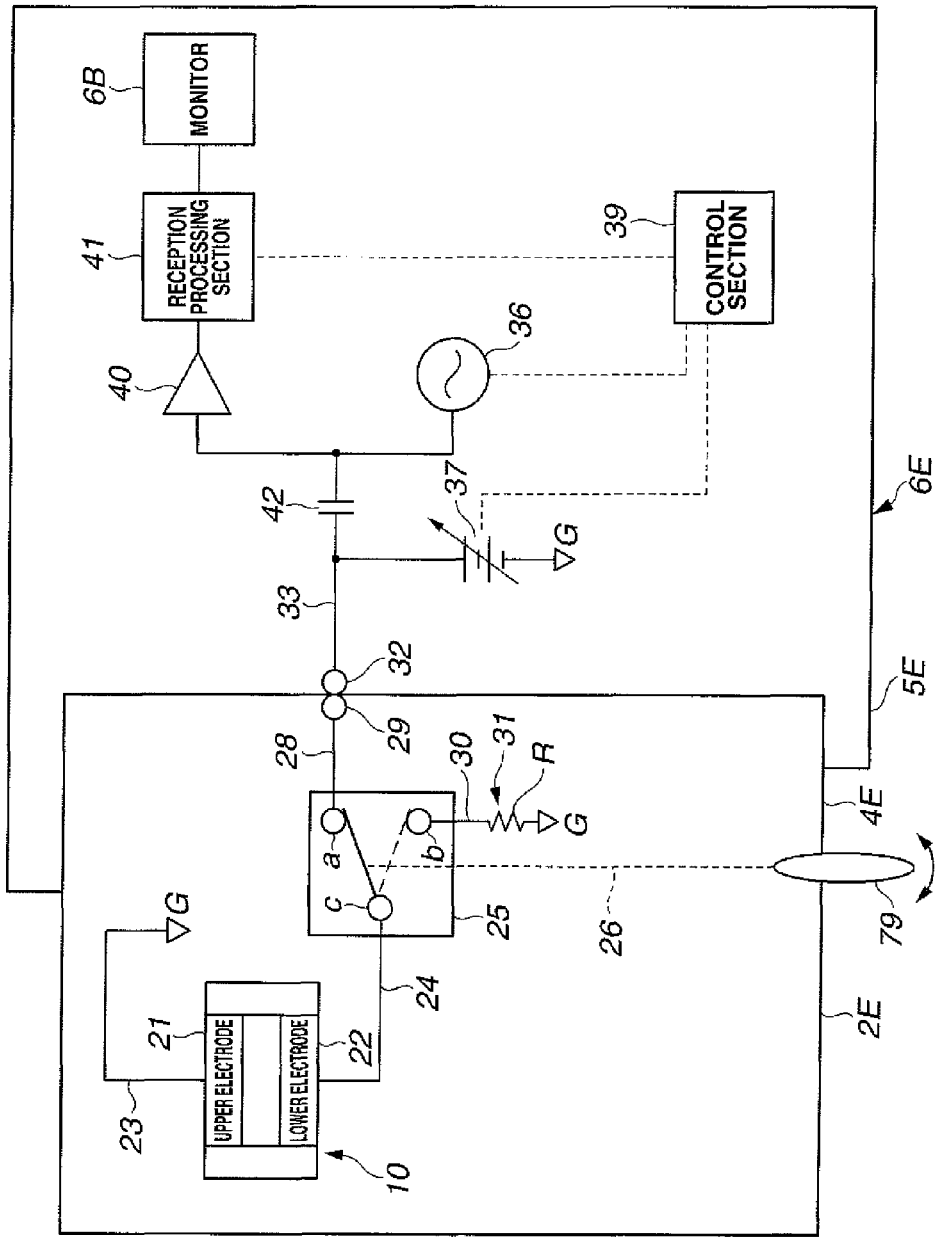
FIG. 14 is a configuration diagram illustrating a configuration of an ultrasound probe unit and an observation apparatus according to a fifth embodiment of the present invention.

FIG. 14 illustrates a configuration example of, for example, a mechanical scan ultrasound probe unit 2E and an observation apparatus 6E according to a fifth embodiment of the present invention. The present embodiment adopts, for example, a connector 4E and a connector receiver 5E as a connection section different from that in the first embodiment.

As shown in FIG. 14, the ultrasound probe unit 2E is mounted with one C-MUT 10 having the same configuration as that shown in FIG. 2A. Furthermore, as shown in FIG. 2A, a connection contact 32 in the observation apparatus 6E is connected to a DC bias voltage generation section 37 via a signal line 33.

Figure 15A:
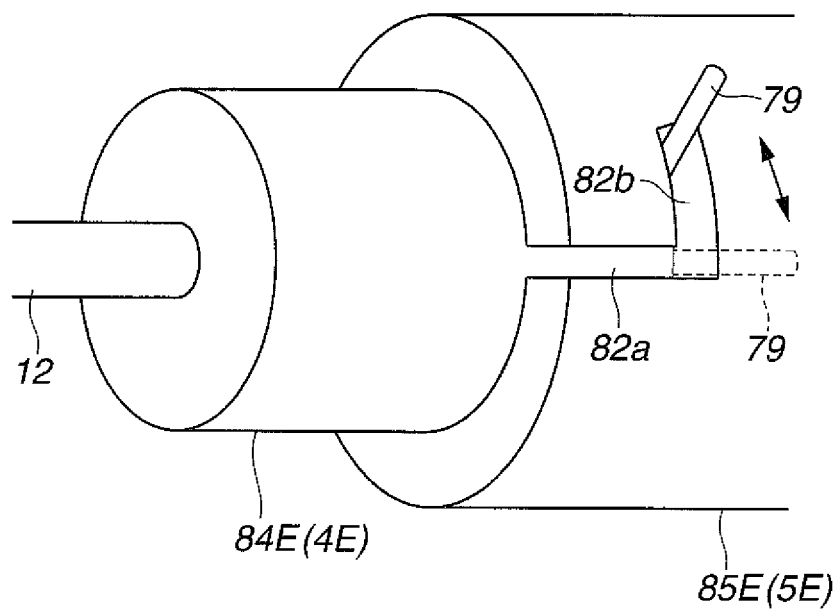
FIG. 15A is a perspective view illustrating a locked state in which the connector of the ultrasound probe unit in FIG. 14 is connected and fixed to the connector receiver of the observation apparatus.

In the present embodiment, as shown in FIG. 15A, the connector 4E and the connector receiver 5E have a cylindrical connector housing (simply referred to as "housing") 84E and a connector receiver housing (simply referred to as "housing") 85E provided with a columnar concave section with which the cylindrical housing 84E is engaged.

A connection contact 29 is provided on a front end face of the housing 84E in FIG. 14 and the connection contact 32 which is in contact with and electrically connected to the connection contact 29 is provided on an innermost part of the concave section in the housing 85E.

Furthermore, a rotatable lever 79 protrudes from a cylindrical side of the housing 84E. On the other hand, the housing 85E of the connector receiver 5E is provided with a guide groove 82*a* which serves as a guide when the housing 84E of the connector 4E is connected/disconnected (attached/detached).

Furthermore, the housing 85E is provided with a circumferential groove 82*b* formed in a direction orthogonal to the guide groove 82*a* for a contact switching operation by the lever 79, setting the connector 4E and the connector receiver 5E in a locked state in conjunction with the switching operation and changing the locked state to a released state.

As is clear from FIG. 15A, when the lever 79 enters the circumferential groove 82*b* side from a position shown by a dotted line (released position), a locked state is in place in which it is possible to prevent (regulate) disconnection of the connector 4E from the connector receiver 5E through pulling out thereof.

Figure 15B:
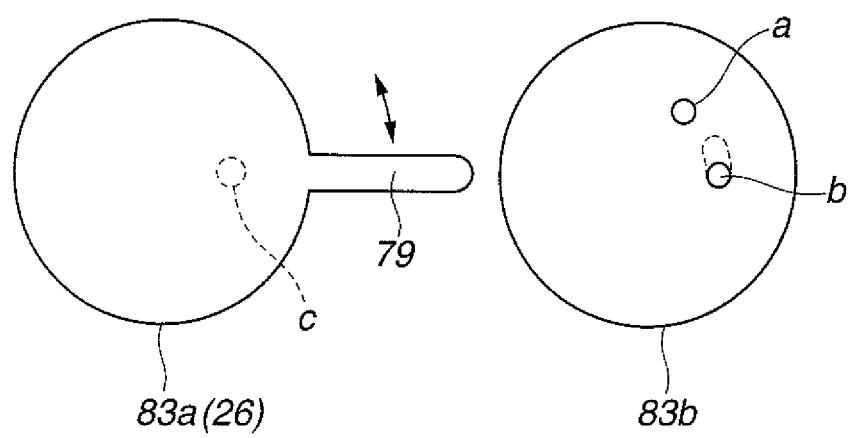
FIG. 15B is a diagram illustrating a rotor side disk connected to the rotary lever and a stator side disk that contacts the rotor side disk, arranged inside the connector.

The proximal end side of the lever 79 is connected to a rotor-side disk 83*a* arranged inside the housing of the connector 4E and rotated as shown in FIG. 15B to form a connection section 26 and a common contact c which forms a switch 25 connected to a signal line 24 is provided on one surface (back surface in FIG. 15B) of the rotor-side disk 83*a*.

Opposite to the rotor-side disk 83*a*, a stator-side disk 83*b* that contacts the rotor-side disk 83*a* is arranged, and a contact a and a contact b that selectively contact and are electrically connected to the common contact c through the turning operation of the lever 79 are formed in the stator-side disk 83*b*.

Both disks 83*a* and 83*b* are formed of an insulating member. Furthermore, signal lines connected to the contacts a and b, and the common contact c are omitted in FIG. 15B.

In the position (lock position) of the lever 79 shown by a solid line in FIG. 15A, the common contact c is electrically connected to the contact a as shown in FIG. 14. This lock position becomes a predetermined mounting state when the connector 4E and the connector receiver 5E are used connected together.

On the other hand, in the position (released position) of the lever 79 shown by the dotted line in FIG. 15A, the common contact c is set to a state in which the common contact c is electrically connected to the contact b as shown by a dotted line in FIG. 14. Furthermore, there is such a structure that the connector 4E cannot be disconnected from the connector receiver 5E unless the lever 79 is set to the released position as described above.

Furthermore, as will be described in later operation, the present embodiment can realize a structure provided with the function described in the third embodiment.

Next, operation of the present embodiment will be described.

When the ultrasound probe unit 2E is used, connected to the observation apparatus 6E to perform an ultrasound inspection, the connector 4E is engaged with the connector receiver 5E and the lever 79 is then set to a lock position. As shown in FIG. 14, the common contact c of the switch 25 is electrically connected to the contact a.

Therefore, the C-MUT 10 of the ultrasound probe unit 2E is ready to be driven by the observation apparatus 6E. A transmission signal from a transmission signal generation section 36 is then superimposed on a DC bias voltage via the signal line 33 and outputted to the ultrasound probe unit 2E side.

As shown in FIG. 14, since the common contact c is electrically connected to the contact a, a transmission signal is superimposed on the DC bias voltage and applied to the lower electrode 22 of the C-MUT 10 and the C-MUT 10 transmits ultrasound to the subject side in the body cavity.

Ultrasound reflected by a part of the subject where an acoustic impedance is changing is received by the C-MUT 10 and becomes an echo signal.

The echo signal superimposed on the DC bias voltage passes through the switch 25, the DC bias voltage thereof is cut by the capacitor 42 and the signal is amplified by the amplifier 40. The echo signal amplified by the amplifier 40 is subjected to signal processing by the reception processing section 41, converted to a video signal, and then outputted to the monitor 6B and an ultrasound tomographic image is displayed on the display screen of the monitor 6B.

After performing the ultrasound inspection using ultrasound, the operator turns OFF the power to the observation apparatus 6E to stop the function of transmitting/receiving ultrasound (and the function of generating a DC bias voltage).

When the ultrasound probe unit 2E is disconnected from the observation apparatus 6E, the lever 79 is turned to a released position shown by the dotted line in FIG. 15A, and it is thereby possible to disconnect the connector 4E of the ultrasound probe unit 2E from the connector receiver 5E of the observation apparatus 6E.

In conjunction with the turning of the lever 79 in this case, the common contact c of the switch 25 is connected to the contact b, that is, a resistor R making up a discharge section 31 via the connection section 26. As a result, the charge of the C-MUT 10 is discharged to ground in FIG. 14 via the resistor R of the discharge section 31. It is thereby possible to eliminate the charge present in the C-MUT 10.

Therefore, according to the present embodiment (since the charge present in the C-MUT 10 can be eliminated), it is possible to reliably prevent deterioration of the contact due to discharge when the connector 4E is disconnected from the connector receiver 5E caused by the charge present in the C-MUT 10 or eliminate the possibility that a high voltage during discharge may damage the transmission/reception processing system that performs transmission/reception in the observation apparatus 6E.

Furthermore, according to the present embodiment, it is possible to reduce or prevent the advance of deterioration of the C-MUT 10 device itself due to the charge accumulated for a long time in the capacitive micromachined ultrasonic transducer (C-MUT) 10. The present embodiment prevents the charge from being accumulated in the C-MUT 10 device, and can thereby secure stable sensitivity for a long period of time. The present embodiment can also realize an ultrasound diagnostic system with a high level of reproducibility.

Furthermore, according to the present embodiment, the connector 4E cannot be disconnected from the connector receiver 5E when the connector 4E is connected to the connector receiver 5E and the lever 79 is set to a lock position, it is thereby possible to reliably prevent the ultrasound probe unit 2E from being carelessly disconnected from the observation apparatus 6E during an ultrasound inspection. The present embodiment can provide an ultrasound diagnostic system with a high level of operability and reliability.

Furthermore, the present embodiment may be adapted to have a configuration having effects similar to those of the aforementioned third embodiment. For example, instead of the circular contact b shown by the solid line in FIG. 15B, an arc-shaped contact that extends in the direction of the contact a as shown by a two-dot dashed line may be adopted.

When the lever 79 is turned from the lock position corresponding to a predetermined mounting state to a released position, adopting such an arc-shaped contact causes the common contact c to have an electric connection (continuity) with the arc-shaped contact slightly before the lever 79 is set to the released position. The electric connection thereof is maintained until the lever 79 is set to the released position.

Therefore, when the operator sets the ultrasound probe unit 2E to a released position (of the connection section) where the ultrasound probe unit 2E can be disconnected from the observation apparatus 6E, the C-MUT 10 is electrically connected to the discharge section 31 in the connection state of the switch 25 at the released position.

In this state, the charge between the lower electrode 22 and the upper electrode 21 of the C-MUT 10 is discharged by the discharge section 31 and the contact a of the switch 25 (connected to the connection contact 29 of the connector 4E) is in a released state, and it is thereby possible to disconnect the ultrasound probe unit 2E from the observation apparatus 6E without any problem, that is, without causing any adverse influence on the transmission/reception processing system or the like of the observation apparatus 6E.

An embodiment formed by partially combining the configurations of the aforementioned embodiments or the like also belongs to the present invention.

What is claimed is:

1. An ultrasound diagnostic system comprising:
   an ultrasound device comprising:
      a capacitive micromachined ultrasonic transducer comprising a first electrode and a second electrode facing each other;
      a connector; and
      a discharge device configured to discharge charge accumulated between the first electrode and the second electrode of the capacitive micromachined ultrasonic transducer to a ground; and
   an ultrasound observation apparatus comprising:
      a transmission/reception processor configured to output a transmission signal to drive the capacitive micromachined ultrasonic transducer, and to perform signal processing on a received signal received by the capacitive micromachined ultrasonic transducer;
      a connector receiver configured to be detachably connected to the connector of the ultrasound device; and
      a DC bias voltage generation circuit configured to generate a DC bias voltage to be superimposed on the transmission signal and the received signal;
   wherein the ultrasound device further comprises:
      a switch configured to selectively switch a common electric contact connected to the first electrode between a first electric contact and a second electric contact, wherein:
      the first electric contact is connected with a signal line that transmits the transmission signal and the received signal, on each of which the DC bias voltage is superimposed, and
      the second electric contact is connected with the discharge device, wherein the charge accumulated between the first electrode and the second electrode of the capacitive micromachined ultrasonic transducer is discharged by the discharge device to the ground via the common electric contact connected to the second electric contact; and
   a lock configured to perform:
      a lock operation, when the connector of the ultrasound device is connected to the connector receiver of the ultrasound observation apparatus, to lock the connector and the connector receiver in a locked state in which the connector is prevented from disconnecting from the connector receiver; and
      a release operation to release the connector and the connector receiver into a released state from the locked state such that the connector can be disconnected from the connector receiver;
wherein the switch is configured to switch the common electric contact in conjunction with the lock operation and the release operation of the lock, wherein:
when the lock performs the lock operation, the switch switches the common electric contact to connect to the first electric contact; and
when the lock performs the release operation, the switch switches the common electric contact to connect to the second electric contact such that the charge accumulated between the first electrode and the second electrode of the capacitive micromachined ultrasonic transducer is discharged by the discharge device to the ground via the common electric contact connected to the second electric contact,
wherein the ultrasound diagnostic system further comprises a lever configured to actuate the lock to perform the lock operation and the release operation,
wherein the connector comprises:
a contact pin constituting the common electric contact,
a housing that accommodates a proximal end side of the contact pin, and
a contact pin holding frame provided adjacent to a distal end opening of the housing and configured to hold the contact pin such that the contact pin is movable in a vertical direction which is vertical to a longitudinal direction of the contact pin, and the second electric contact provided on an inner surface near the distal end opening of the housing, the second electric contact contacting the contact pin in the released state, and
wherein the lock is configured to cause the contact pin to disconnect from the second electric contact in conjunction with a movement of the contact pin holding frame in the vertical direction by the turning operation of the lever in the released state, and further to cause a distal end of the contact pin to mechanically connect to a contact pin receiver constituting the first electric contact provided to the connector receiver when the connector is connected to the connector receiver after the movement of the contact pin in the vertical direction.

2. The ultrasound diagnostic system according to claim 1, wherein the discharge device comprises a resistor, wherein the charge accumulated between the first electrode and the second electrode of the capacitive micromachined ultrasonic transducer is discharged via the resistor to the ground.

3. The ultrasound diagnostic system according to claim 1, further comprising:
a display processor configured to generate a video signal for reporting the state of the switch to the ultrasound observation apparatus and allowing the state of the switch to be displayed on a display.

4. The ultrasound diagnostic system according to claim 1, further comprising:
a lever configured to actuate the lock to perform the lock operation and the release operation,
wherein in operating the lever to actuate the lock to perform the release operation, the switch is configured to switch the common electric contact to connect to the second electric contact such that the charge accumulated between the first electrode and the second electrode of the capacitive micromachined ultrasonic transducer is discharged by the discharge device to the ground via the common electric contact connected to the second electric contact before the connector is disconnected from the connector receiver.

5. The ultrasound diagnostic system according to claim 1, wherein the capacitive micromachined ultrasonic transducer is an electronic scan capacitive micromachined ultrasonic transducer or a mechanical scan capacitive micromachined ultrasonic transducer.

6. The ultrasound diagnostic system according to claim 1, wherein the switch comprises a switching mechanism that switches the common electric contact to electrically connect to the second electric contact in a middle state where the connector and the connector receiver are brought from the locked state to the released state.

7. An ultrasound diagnostic system comprising:
an ultrasound device comprising:
a capacitive micromachined ultrasonic transducer comprising a first electrode and a second electrode facing each other;
a connector; and
a discharge device configured to discharge charge accumulated between the first electrode and the second electrode of the capacitive micromachined ultrasonic transducer to a ground; and
an ultrasound observation apparatus comprising:
a transmission/reception processor configured to output a transmission signal to drive the capacitive micromachined ultrasonic transducer, and to perform signal processing on a received signal received by the capacitive micromachined ultrasonic transducer;
a connector receiver configured to be detachably connected to the connector of the ultrasound device; and
a DC bias voltage generation circuit configured to generate a DC bias voltage to be superimposed on the transmission signal and the received signal;
wherein the ultrasound device further comprises:
a switch configured to selectively switch a common electric contact connected to the first electrode between a first electric contact and a second electric contact, wherein:
the first electric contact is connected with a signal line that transmits the transmission signal and the received signal, on each of which the DC bias voltage is superimposed, and
the second electric contact is connected with the discharge device, wherein the charge accumulated between the first electrode and the second electrode of the capacitive micromachined ultrasonic transducer is discharged by the discharge device to the ground via the common electric contact connected to the second electric contact; and
a lock configured to perform:
a lock operation, when the connector of the ultrasound device is connected to the connector receiver of the ultrasound observation apparatus, to lock the connector and the connector receiver in a locked state in which the connector is prevented from disconnecting from the connector receiver; and
a release operation to release the connector and the connector receiver into a released state from the locked state such that the connector can be disconnected from the connector receiver;
wherein the switch is configured to switch the common electric contact in conjunction with the lock operation and the release operation of the lock, wherein:
when the lock performs the lock operation, the switch switches the common electric contact to connect to the first electric contact; and
when the lock performs the release operation, the switch switches the common electric contact to connect to the second electric contact such that the charge accumulated between the first electrode and the second electrode of the capacitive micromachined ultrasonic transducer is discharged by the discharge device to the ground via the common electric contact connected to the second electric contact, wherein the ultrasound diagnostic system further comprises:
  a lever configured to actuate the lock to perform the lock operation and the release operation, wherein the connector comprises a rotatable rotor-side disk from which the lever is protruded, and the common electric contact provided on one surface of the rotor-side disk, a position of the common electric contact rotationally moving in conjunction with the turning operation of the lever, and wherein the connector receiver comprises a stator-side disk having a contacting surface which contacts the one surface of the rotor-side disk, the second electric contact provided at a position contacting the common electric contact on the contacting surface in the released state, and the first electric contact provided at a position contacting the common electric contact in the locked state.

* * * * *